United States Patent
Nesbit et al.

(10) Patent No.: US 10,449,019 B2
(45) Date of Patent: Oct. 22, 2019

(54) SYSTEMS AND METHODS FOR SECURING A DENTAL IMPLANT

(71) Applicant: Natural Dental Implants AG, Berlin (DE)

(72) Inventors: Lea Ellermeier Nesbit, Dallas, TX (US); Ruedger Rubbert, Berlin (DE); Andreas Weinrich, Berlin (DE)

(73) Assignee: NATURAL DENTAL IMPLANTS AG, Berlin (DE)

( * ) Notice: Subject to any disclaimer, the term of this patent is extended or adjusted under 35 U.S.C. 154(b) by 27 days.

(21) Appl. No.: 15/625,424

(22) Filed: Jun. 16, 2017

(65) Prior Publication Data

US 2018/0021110 A1    Jan. 25, 2018

Related U.S. Application Data

(60) Provisional application No. 62/364,708, filed on Jul. 20, 2016.

(51) Int. Cl.
*A61C 8/00*    (2006.01)

(52) U.S. Cl.
CPC .......... *A61C 8/0089* (2013.01); *A61C 8/0001* (2013.01); *A61C 8/005* (2013.01); *A61C 8/0036* (2013.01)

(58) Field of Classification Search
CPC ... A61C 8/0089; A61C 8/0001; A61C 8/0087; A61C 8/0036; A61C 8/005; A61C 8/001; A61C 13/12; A61C 13/225; A61C 1/084; A61C 7/08; A61C 5/007
USPC .................................. 433/172–173; 128/861
See application file for complete search history.

(56) References Cited

U.S. PATENT DOCUMENTS

| | | | |
|---|---|---|---|
| 4,869,669 A | 9/1989 | Grubbs | |
| 4,975,053 A | 12/1990 | Hofsess | |
| 5,386,821 A | 2/1995 | Poterack | |
| 5,562,450 A | 10/1996 | Gieloff et al. | |
| D397,442 S | 8/1998 | Kittelsen | |

(Continued)

FOREIGN PATENT DOCUMENTS

| | | |
|---|---|---|
| EP | 2191784 A1 | 6/2010 |
| WO | 2006031096 | 3/2006 |

OTHER PUBLICATIONS

E. Berndt, et al., "Topologically Structured Surfaces and Coating Treatments for Periodontal and Osseo-Integration," Prior Art Publishing Technisches Journal, Mar. 2009 Nr 1A.

(Continued)

*Primary Examiner* — Wade Miles
*Assistant Examiner* — Shannel N Wright
(74) *Attorney, Agent, or Firm* — Bracewell LLP; Constance G. Rhebergen; Kevin R. Tamm

(57) ABSTRACT

A mouthpiece for inserting and securing a push-in-type dental implant in a jawbone bore hole or a natural extraction socket of a patient, related systems, and methods of designing and manufacturing a mouthpiece are disclosed. The mouthpiece can include a first interface to engage with an occlusal portion of the dental implant and at least a second interface to engage with occlusal surfaces of the opponent crowns so that the mouthpiece is operable to securely insert the dental implant into the jawbone bore hole or extraction socket of the patient when an upper jawbone and lower jawbone of a patient are brought together.

19 Claims, 14 Drawing Sheets

(56) References Cited

U.S. PATENT DOCUMENTS

| | | | |
|---|---|---|---|
| 5,897,696 A * | 4/1999 | Giordano | A61L 31/08 106/181.1 |
| 6,099,313 A | 8/2000 | Dorken et al. | |
| 7,090,492 B2 | 8/2006 | Rodriquez De Val | |
| RE43,470 E * | 6/2012 | Wade | A61C 8/0048 433/173 |
| 8,196,587 B2 | 6/2012 | Chodorow | |
| 2003/0217744 A1 | 11/2003 | Sugai et al. | |
| 2010/0203479 A1* | 8/2010 | Bulloch | A61C 1/084 433/215 |
| 2010/0240000 A1* | 9/2010 | Yau | A61C 13/0004 433/37 |
| 2010/0304331 A1 | 12/2010 | Preti et al. | |
| 2011/0086328 A1 | 4/2011 | Wedeking | |
| 2011/0091836 A1* | 4/2011 | Fujii | A61C 1/084 433/75 |
| 2012/0107774 A1 | 5/2012 | Feith | |
| 2013/0059270 A1 | 3/2013 | Zacher | |
| 2013/0130199 A1 | 5/2013 | Palm | |
| 2014/0193771 A1* | 7/2014 | Dolfi | A61C 1/084 433/76 |
| 2014/0322665 A1* | 10/2014 | Fang | A61C 1/084 433/75 |
| 2015/0030993 A1 | 1/2015 | Von Malottki et al. | |
| 2016/0038254 A1* | 2/2016 | Prestipino | A61C 1/084 433/72 |

OTHER PUBLICATIONS

International Search Report, Application No. PCT/EP2017/067714, dated Nov. 6, 2017.

* cited by examiner

SYSTEMS AND METHODS FOR SECURING A DENTAL IMPLANT

PRIORITY CLAIM

The present application is a non-provisional application of and claims the benefit of and priority to U.S. Prov. App. Ser. No. 62/364,708, filed Jul. 20, 2016, the entire disclosure of which is hereby incorporated herein by reference.

BACKGROUND

Field

The present disclosure relates generally to the field of dentistry, and more particularly to the field of dental restorations, implants, and prostheses. The disclosure further relates to systems and methods for comfortably securing a dental implant into the jawbone of a patient.

Description of Related Art

Human teeth serve a variety of functions. Not only are they important for chewing food, but they are also necessary to properly pronounce certain consonants, especially fizzle- and S-sounds. Furthermore, teeth play a major role in our personal appearance. Healthy and well aligned teeth are an ideal of beauty and appear as a cosmetic sign of youth and success.

Although various preventive measures, like frequent tooth brushing, flossing, and drinking fluoridated or iodized water are widely accepted and used, the great majority of people are sooner or later challenged with dental fillings, restorations, implants, and/or other prostheses.

A major goal in dentistry is to postpone loss of teeth as long as possible. Another goal is certainly to provide comfortable prostheses with a broad scope/indication and a long lasting life-time.

Generally, the number of available restorative and prosthetic options is limited. Typically, fillings, inlays, and crowns are used if the root and its embedding periodontal structure are healthy, and sufficient as support for such restorative partial prostheses. Traditionally, if an original tooth could no longer be used, the the use of bridges or non-customized osseointegrated implants was recommended. In this context, several negative aspects are to be endured. In order to provide the support structure for a bridge, adjacent teeth are ground, and healthy enamel is partially destroyed. With osseointegrated implants, the gingiva-implant interface is often the cause of chronic local infection. Removable dentures, which are generally considered the final prosthetic option, have severe functional limitations and significant maintenance requirements.

There are many methods or options for replacing missing teeth. Off-the-shelf or pre-shaped osseointegrated dental implants are one of the options. Osseointegration means the direct contact of the implant surface with the bone without a fibrous connective tissue interface (natural teeth are typically not in direct contact with the bone, but are connected to the bone by ligaments). The use of such dental implants includes a wide variety of implant designs and materials, use of implants in different locations in the mouth, and use of a variety of surgical protocols.

Endosteal, also called endosseous implants, are placed into the bone like natural tooth roots. They can provide an anchor for one or more artificial teeth and/or crowns. They are the most commonly used type of implants. There are various types of endosteal implants, for example, screws, cylinders, cones, plates and blades. The generic screw, cylinder, and cone types of implants are sometimes called "root-form" type. Such generic root-form implants that replace a single tooth generally consist of three parts, the actual implant-root for osseointegration, an abutment, and the artificial crown. The interfaces between the three aforementioned parts are critical in respect to the sealing quality between said three parts. Bacterial infections can be caused if the sealing is compromised in regards to its short, mid and long-term stability.

Such three-part implant designs have a first sub-gingival joint between the implant screw and the abutment. The first joint is, with regard to height, placed adjacent to the bone crest of the jaw of the implant-receiving patient. The second joint is placed iso- or supra-gingival, which means on the same vertical height of the mouth facing surface of the gingiva or beyond the trans-gingival portion of the overall implant design. The first joint between the implant screw and abutment is especially under the static and dynamic stress of mastication forces, and is identified as an area where bacteria may congregate, causing a chronic infection. This chronic infection of the adjacent bone is sometimes called "periimplantitis."

Sometimes implant designs that actually consolidate two of said three parts (e.g., the implant-root to be osseointegrated and the abutment) are referred to as one-piece implants. Contrary hereto, the term "one-piece" implant as used hereinafter is meant to refer to the integration of all three parts: the implant root, the abutment, and the crown. The term "immediate placing" of an implant is used if the integration of the implant into the jaw occurs a short term after the extraction of a tooth.

If such implants have a reasonable initial contact stability with the bone directly after being inserted (referred to as primary stability), then such implants are available for so called "immediate load", which means that the osseo-integrative stability, or secondary stability, does not need to be developed before performing the following process steps: making an impression of the abutment part of the implant in conjunction with the gingiva and the adjacent teeth situation, then fabricating the crown, implementing the crown, and actually allowing the patient to use the implant for functional load, including mastication.

Subperiosteal implants are implants that are placed over the bone in cases where the bone has atrophied and jaw structure is limited. Subperiosteal implants are customized metal frameworks, providing the equivalent of multiple tooth roots. They can be applied in a limited area or in the entire mouth. After application, natural tissue membrane and/or bone will grow back around the implant, thus providing more stability. Posts are positioned to protrude through the gum to hold the prosthesis.

Traditionally, submerged osseointegrated dental implants are placed in bone and covered by mucosa during the immediate post-operative healing period. At four to six months, a second surgical procedure is performed to expose the implant so it may be loaded first with various types of abutments and second with various types of dental crowns. In recent years, immediate non-submerged implant placement following tooth extraction and immediate abutment and crown loading after surgical placement has become more common.

Generic ceramic dental implants are available and made from yttria-stabilized tetragonal zirconia polycrystal (Y-TZP) ceramics. Although such ceramic materials are, due to the internal crystal structure and mechanisms, able to suppress micro-cracks, it has been reported in the industry that in the moist and warm environment of the human body, the long term stability of Y-TZP ceramics and conventional dental implants is considered compromised to the extent that respective dental implants cannot be considered fracture-safe for the life-time expectations established.

The success rate and the in-vivo lifetime of non-customized osseointegrated dental implants are limited, and the surgical procedure is heavily invasive, because in most cases an osteotomy is performed, where bone needs to be drilled or ground in order to be adapted to the shape of the non-customized implants. Usually, generic root-form implants have one or more helical ridges or male threads on the outside and are screwed into a borehole in the jawbone with a screw ratchet. There are also push-in-type cylindrical or conical dental implants available that are initially pushed and then hammered into position in a cylindrical or conical borehole artificially created in the jawbone.

Alternatively, custom-shaped dental implants are made to fit a natural extraction socket of a patient. In order to securely fit such a naturally-tooth-root-shaped implant, dentists oftentimes must hammer the implant into the jawbone extraction socket after the jawbone socket is prepared and cleaned for osseointegration. Such hammering is disconcerting to patients and causes vibrations throughout a patient's body, even when local or general anesthetic has been applied. Both the screw connection of the dental implant with the jawbone or the press-fit that is based on friction and compression between the dental implant and the artificially made or natural extraction bone socket serve the function of primary stability, while long term stability on either implant type is based on a bonding connection between bone and the implant material and on the bone growing tightly into the roughness of the implant surface topography.

Furthermore, osseointegrated implants are a limiting factor in a later orthodontic treatment. Problems relating to nerve transposition, osseous grafting, ridge augmentation, and sinus augmentation of osseointegrated dental implants, and/or to tissue health adjacent to dental implants have also been reported. Patients often complain about chronically infected periodontal structure caused by osseointegrated implants.

In cases where a tooth is not severely damaged, and would be ready to receive a partial restoration but an intra-oral repair is impossible due to access problems, or a reverse root canal treatment is required, an alternative method is intentional re-implantation. The tooth is extracted, repaired, and re-integrated into the existing periodontal or perio-type structure of a dental patient. A disadvantage relating to such techniques is certainly that the specific tooth to be re-implanted or transplanted still needs an overall reasonable condition and prognosis to justify an intentional re-implantation, and only certain root and root canal deficiencies can be repaired this way.

U.S. Pat. No. 5,562,450 references the German application DE 27 29 969 A1, incorporated herein by reference in its entirety, which describes osseointegration of an implant that is substantially a copy of an extracted human tooth fabricated by a process involving copy milling. In order to be successfully osseointegrated, the connective tissue (e.g., ligament) remaining in the extraction socket needs to be removed by being scraped out or curetted. The '450 patent recognizes the need to create a compression pressure between the bone and the implant in order to reach reasonable primary stability of the implant and teaches to dimensionally enlarge the anatomical shape of the implant over the extracted tooth to fill the extraction socket.

Rubbert and Berndt reference in the article "Topologically Structured Surfaces and Coating Treatments for Periodontal and Osseo-Integration" published on Apr. 7, 2009, which is incorporated herein by reference in its entirety, various aspects of surface condition and treatments of dental implants and prostheses.

U.S. Pat. No. 6,099,313 discloses a dental implant for osseointegration having a bone-contact section which is root-shaped with an apical extension and an abutment described as a build-up section for fastening a crown.

All such restorative and prosthetic options and methodologies are deficient, being heavily invasive and/or limited in their respective scope. There has not been recognition, until now by the inventors, of the need for products, systems, and methods related to the securing and integration of dental implants into the jawbone structure of patients, which reduce or eliminate the need for hammering or other jarring, forceful external means.

The product, and related systems and methods provided by embodiments of the present invention or inventions comprise several independent inventive features providing substantial improvements to conventional devices and processes. The greatest benefit will be achieved for dental treatments, especially for patients requiring tooth replacement.

SUMMARY

In view of the foregoing, various embodiments of the present invention beneficially provide customized mouthpiece apparatus and methods for inserting and securing push-in type non-customized or custom-shaped dental prostheses and implants.

Therefore, disclosed herein is a mouthpiece for inserting and securing a dental implant root portion in a jawbone of a patient. The mouthpiece includes a protrusion, wherein the protrusion is operable to engage with at least a portion of a dental tooth prosthesis when the dental tooth prosthesis is placed proximate a dental cavity into which the dental tooth prosthesis will be secured, and wherein the dental tooth prosthesis includes the dental implant root portion. The mouthpiece also includes a support structure, wherein the support structure is engaged with the protrusion, wherein the support structure is operable to engage at least one pre-existing dental structure in the patient's mouth when an upper jawbone and lower jawbone of the patient are spaced apart allowing for space between a first pre-existing dental structure on the upper jawbone of the patient and a second pre-existing dental structure on the lower jawbone of the patient, wherein the support structure stably supports the protrusion when the upper jawbone and lower jawbone are brought together, wherein the protrusion extends outwardly from the support structure, and wherein the mouthpiece is operable to securely insert the dental implant root portion into the jawbone of the patient when the upper jawbone and lower jawbone are brought together.

In one example embodiment, the protrusion is operable to engage with an occlusally-facing surface of the dental implant root portion of the dental tooth prosthesis. In some embodiments, the protrusion may form a form-locking fit with the occlusally-facing surface of the dental implant root portion of the dental tooth prosthesis, the protrusion including a recessed portion shaped as a substantial negative of the occlusally-facing surface. In certain embodiments, the protrusion may be operable to engage with a crown of the dental tooth prosthesis. In other embodiments, the protrusion may form a form-locking fit with the crown of the dental tooth prosthesis, the protrusion including a recessed portion shaped as a substantial negative of the crown. In some embodiments, the protrusion and the support structure may be monolithically formed as one piece.

In one example embodiment, the support structure is operable to engage at least one crown located in the same jawbone in which the dental cavity, into which the dental tooth prosthesis will be secured, is located. In certain embodiments, the support structure may be operable to engage at least one crown adjacent to the dental cavity into which the dental tooth prosthesis will be secured. In yet other embodiments, the support structure may be custom form-fitted to engage the at least one crown.

Still in other embodiments, the support structure may be operable to engage at least one crown located in the jawbone opposite the jawbone in which the dental cavity, into which the dental tooth prosthesis will be secured, is located. In some embodiments, the support structure may be operable to align the protrusion with the dental tooth prosthesis. Still in other embodiments, the support structure may be custom form-fitted to engage the at least one crown. In other embodiments, the support structure may be operable to engage pre-existing dental structures on both the upper jawbone and lower jawbone of the patient.

Still in certain embodiments, the support structure may be custom form-fitted to engage pre-existing dental structures on both the upper jawbone and lower jawbone of the patient. In some embodiments, the pre-existing dental structures may include crowns of the patient. Still in other embodiments, the protrusion may be operable to engage with an occlusally-facing surface of the dental implant root portion of the dental tooth prosthesis. The protrusion may form a form-locking fit with the occlusally-facing surface of the dental implant root portion of the dental tooth prosthesis, the protrusion including a recessed portion shaped as a substantial negative of the occlusally-facing surface, in some embodiments. In other embodiments, the protrusion may be operable to engage with a crown of the dental tooth prosthesis. In further embodiments, the protrusion may form a form-locking fit with the crown of the dental tooth prosthesis, the protrusion including a recessed portion shaped as a substantial negative of the crown.

In one example embodiment, the support structure substantially matches a pre-existing dental layout of the patient's mouth, and the support structure is operable to form a form-locking fit with the pre-existing dental layout of the patient's mouth. In some embodiments, the dental tooth prosthesis is a one-piece dental tooth prosthesis including the dental implant root portion and a crown. Still in other embodiments, the protrusion extends outwardly from the support structure substantially perpendicular to a plane formed by the support structure.

Another example embodiment is a method for forming a mouthpiece for inserting and securing a dental implant root portion in a jawbone of a patient. The method includes acquiring shape data from the patient's mouth, at least a portion of the shape data including in vivo shape data of at least one pre-existing dental structure in the patient's mouth, forming a support structure, wherein the support structure is operable to engage the at least one pre-existing dental structure in the patient's mouth when an upper jawbone and lower jawbone of the patient are spaced apart allowing for space between a first pre-existing dental structure on the upper jawbone of the patient and a second pre-existing dental structure on the lower jawbone of the patient, and forming a protrusion to be engaged with the support structure, wherein the support structure stably supports the protrusion when the upper jawbone and lower jawbone are brought together, wherein the protrusion is operable to engage with at least a portion of a dental tooth prosthesis, the dental tooth prosthesis including the dental implant root portion, when the dental tooth prosthesis is placed proximate a dental cavity into which the dental tooth prosthesis will be secured, wherein the protrusion extends outwardly from the support structure substantially perpendicular to a plane formed by the support structure, and wherein the protrusion is operable to securely insert the dental implant root portion into the jawbone of the patient when the upper jawbone and lower jawbone are brought together.

In one example embodiment, the step of forming the protrusion includes forming the protrusion to engage with an occlusally-facing abutment or surface of the dental implant root portion of the dental tooth prosthesis. In some embodiments, the step of forming the protrusion includes forming the protrusion to make a form-locking fit with the occlusally-facing abutment of the dental implant root portion of the dental tooth prosthesis, the protrusion including a recessed portion shaped as a substantial negative of the occlusally-facing abutment. Still in other embodiments, the step of forming the protrusion includes forming the protrusion to engage with a crown of the dental tooth prosthesis.

In some embodiments, the step of forming the protrusion includes forming the protrusion to make a form-locking fit with the crown of the dental tooth prosthesis, the protrusion including a recessed portion shaped as a substantial negative of the crown. In certain embodiments, the steps of forming the support structure and forming the protrusion result in a monolithically-formed mouthpiece for inserting and securing the dental implant root portion. Still in other embodiments, the step of forming the support structure includes forming the support structure to engage at least one crown located in the same jawbone in which the dental cavity, into which the dental tooth prosthesis will be secured, is located. In some embodiments, the step of forming the support structure includes forming the support structure to engage at least one crown adjacent to the dental cavity into which the dental tooth prosthesis will be secured.

In certain embodiments, the step of forming the support structure includes forming the support structure to custom form-fit the at least one crown. In other embodiments, the step of forming the support structure includes forming the support structure to engage at least one crown located in the jawbone opposite the jawbone in which the dental cavity, into which the dental tooth prosthesis will be secured, is located.

In one example embodiment, the step of forming the support structure includes forming the support structure to align the protrusion with the dental tooth prosthesis. Still in other embodiments of the method, the step of forming the support structure includes forming the support structure to custom form-fit the at least one crown. In some instances, the step of forming the support structure includes forming the support structure to engage pre-existing dental structures on both the upper jawbone and lower jawbone of the patient. In other embodiments, the step of forming the support structure includes forming the support structure to custom form-fit pre-existing dental structures on both the upper jawbone and lower jawbone of the patient.

The pre-existing dental structures can include crowns of the patient. In some embodiments, the step of forming the protrusion includes forming the protrusion to engage with an occlusally-facing abutment or surface of the dental implant root portion of the dental tooth prosthesis. Still in other embodiments, the step of forming the protrusion includes forming the protrusion to include a form-locking fit with the occlusally-facing abutment or surface of the dental implant root portion of the dental tooth prosthesis, the protrusion including a recessed portion shaped as a substantial negative of the occlusally-facing abutment.

The step of forming the protrusion can include forming the protrusion to engage with a crown of the dental tooth prosthesis. In some embodiments, the step of forming the protrusion includes forming the protrusion to make a form-locking fit with the crown of the dental tooth prosthesis, the protrusion including a recessed portion shaped as a substantial negative of the crown. In certain embodiments, the step of forming the support structure includes forming the support structure to substantially match a pre-existing dental layout of the patient's mouth, and forming the support structure to form a form-locking fit with the pre-existing dental layout of the patient's mouth. The dental tooth prosthesis is a one-piece dental tooth prosthesis including the dental implant root portion and a crown, in some embodiments. The shape data from the patient's mouth can include virtual shape data on a computer readable medium.

In one example embodiment, the steps of forming the support structure and forming the protrusion further include the steps of deriving a virtual support structure from the shape data, deriving a virtual protrusion from the shape data and from shape data describing the dental tooth prosthesis, virtually modifying at least a portion of at least one of the virtual support structure or the virtual protrusion, and virtually defining a virtual mouthpiece including the virtual support structure and the virtual protrusion, wherein the virtual mouthpiece substantially represents the mouthpiece for inserting and securing the dental implant root portion.

Another example embodiment is a method for inserting and securing a dental implant root portion in a jawbone of a patient. The method includes removing a dental component from the patient's mouth, the dental component including a dental component root portion, wherein the dental component root portion is embedded in a cavity of the jawbone of the patient, preparing the cavity for insertion of a dental tooth prosthesis, wherein the dental tooth prosthesis includes a dental implant root portion, setting the dental tooth prosthesis proximate the cavity for inserting and securing the dental tooth prosthesis by a mouthpiece, the mouthpiece including a protrusion, wherein the protrusion is operable to engage with at least a portion of the dental tooth prosthesis when the dental tooth prosthesis is placed proximate the dental cavity into which the dental tooth prosthesis will be secured, a support structure, wherein the support structure is engaged with the protrusion, wherein the support structure is operable to engage at least one pre-existing dental structure in the patient's mouth when an upper jawbone and lower jawbone of the patient are spaced apart allowing for space between a first pre-existing dental structure on the upper jawbone of the patient and a second pre-existing dental structure on the lower jawbone of the patient, wherein the support structure stably supports the protrusion when the upper jawbone and lower jawbone are brought together, wherein the protrusion extends outwardly from the support structure substantially perpendicular to a plane formed by the support structure, and wherein the protrusion is operable to securely insert the dental implant root portion into the jawbone of the patient when the upper jawbone and lower jawbone are brought together, and bringing the upper jawbone and lower jawbone of the patient together to securely insert the dental tooth prosthesis.

In one example embodiment, the protrusion is operable to engage with an occlusally-facing abutment or surface of the dental implant root portion of the dental tooth prosthesis. In some embodiments, the protrusion may form a form-locking fit with the occlusally-facing abutment or surface of the dental implant root portion of the dental tooth prosthesis, the protrusion including a recessed portion shaped as a substantial negative of the occlusally-facing abutment. In other embodiments, the protrusion may be operable to engage with a crown of the dental tooth prosthesis. In certain embodiments, the protrusion may form a form-locking fit with the crown of the dental tooth prosthesis, the protrusion including a recessed portion shaped as a substantial negative of the crown.

The protrusion and the support structure are monolithically formed as one piece, in some embodiments. In other embodiments, the support structure is operable to engage at least one crown located in the same jawbone in which the dental cavity, into which the dental tooth prosthesis will be secured, is located. Still in other embodiments, the support structure is operable to engage at least one crown adjacent to the dental cavity into which the dental tooth prosthesis will be secured. In some embodiments, the support structure is custom form-fitted to engage the at least one crown. Still in yet further embodiments, the support structure is operable to engage at least one crown located in the jawbone opposite the jawbone in which the dental cavity, into which the dental tooth prosthesis will be secured, is located. In certain embodiments, the support structure is operable to align the protrusion with the dental tooth prosthesis. Still in other embodiments, the support structure is custom form-fitted to engage the at least one crown. And, in yet other embodiments, the support structure is operable to engage pre-existing dental structures on both the upper jawbone and lower jawbone of the patient.

Still in some other embodiments, the support structure is custom form-fitted to engage pre-existing dental structures on both the upper jawbone and lower jawbone of the patient. In some embodiments, the pre-existing dental structures include crowns of the patient. In certain instances, the protrusion is operable to engage with an occlusally-facing abutment or surface of the dental implant root portion of the dental tooth prosthesis. Still in alternative embodiments, the protrusion forms a form-locking fit with the occlusally-facing abutment or surface of the dental implant root portion of the dental tooth prosthesis, the protrusion including a recessed portion shaped as a substantial negative of the occlusally-facing abutment. The protrusion is operable to engage with a crown of the dental tooth prosthesis, in some embodiments. In some instances, the protrusion forms a form-locking fit with the crown of the dental tooth prosthesis, the protrusion including a recessed portion shaped as a substantial negative of the crown. In some embodiments, the support structure substantially matches a pre-existing dental layout of the patient's mouth, and the support structure is operable to form a form-locking fit with the pre-existing dental layout of the patient's mouth. The dental tooth prosthesis is a one-piece dental tooth prosthesis including the dental implant root portion and a crown, in some embodiments.

The method may also include the step of temporarily securing at least a portion of the support structure proximate the dental tooth prosthesis to support the dental tooth prosthesis and allow for integration of the dental implant root portion into the jawbone.

Another example embodiment is a mouthpiece, for inserting and securing an implant root portion of a dental tooth prosthesis in a first jawbone of a patient. The mouthpiece includes a first interface surface, and a second interface surface, the first interface surface is operable to engage with an occlusal-facing portion of the dental tooth prosthesis and the second interface surface is operable to engage with an occlusal-facing portion of a pre-existing opponent dental anatomy of a second jawbone of the patient opposite the first jawbone, when the dental tooth prosthesis and the mouthpiece are placed proximate a dental cavity of the first jawbone into which the dental tooth prosthesis will be secured so that the mouthpiece is operable to securely insert the dental implant root portion into the jawbone of the patient when the upper jawbone and lower jawbone are brought together. The first interface surface has a three-dimensional shape and extension operable to align the dental tooth prosthesis with the mouthpiece. The second interface surface has three-dimensional shape and extension operable to align the mouthpiece with the pre-existing opponent dental anatomy. In some embodiments, the mouthpiece may also include a third interface, the third interface surface is operable to engage with an occlusal-facing portion of a pre-existing adjacent dental anatomy of the first jawbone adjacent the dental cavity, so that the mouthpiece is operable to align the first jawbone with the second jawbone when the upper jawbone and lower jawbone are brought together.

Another example embodiment is a system for dental rehabilitation including a dental prosthesis having a push-in type implant root portion to be inserted in a bone cavity of a jawbone of a pre-identified patient, and a mouthpiece for inserting and securing the push-in type implant root in the bone cavity, the mouthpiece including a first interface portion three-dimensionally sized and shaped to receive an occlusal-facing portion of the dental prosthesis, a second interface portion three-dimensionally sized and shaped to receive a first occlusal-facing portion of a first dental anatomy, and a third interface portion three-dimensionally sized and shaped to receive forces from a second occlusal-facing portion of a second dental anatomy of a jawbone opposite the dental cavity when the dental tooth prosthesis and the mouthpiece is placed proximate the dental cavity and proximate the second dental anatomy of the jawbone opposite the dental cavity so that the mouthpiece is operable to securely align and insert the dental implant root portion into the jawbone of the patient when the jawbone with the dental cavity and the jawbone opposite the dental cavity are brought together.

In some embodiments, the third interface portion includes the second interface portion of the mouthpiece, the second occlusal-facing portion includes the first occlusal-facing portion, and the second dental anatomy comprises the first dental anatomy, and the first dental anatomy includes at least one crown opponent to the bone cavity. In some embodiments, the size and the shape of the second interface surface is operable to guide the mouthpiece when the jawbone with the dental cavity and the jawbone opposite the dental cavity are brought together. In certain embodiments, the second dental anatomy is at least one portion of at least one crown adjacent the dental cavity. The size and the shape of the second interface surface is operable to guide the mouthpiece when the jawbone with the dental cavity and the jawbone opposite the dental cavity are brought together, in some embodiments.

Another example embodiment is a method for designing a mouthpiece for inserting and securing an implant root portion of a dental prosthesis in bone cavity of a jawbone of a patient. The method includes receiving first data representing a three-dimensional surface portion of the dental prosthesis, receiving second data representing three-dimensional image data of the dental cavity and three-dimensional image data of a first dental anatomy adjacent the dental cavity, receiving third data representing a three-dimensional image data of a second dental anatomy opposite the dental cavity, receiving a fourth data representing a three-dimensional image data of a dental bite situation including an orientation and a position between the first dental anatomy and the second dental anatomy, deriving a design data forming a virtual model of the mouthpiece responsive to the first data, the second data, the third data, and the forth data.

In some embodiments, the method may also include visualization data including a spatial alignment of a virtual model of the dental prosthesis with a virtual model of the dental cavity, a spatial alignment of the virtual model of the mouthpiece with the virtual model of the dental prosthesis, and a spatial alignment of the virtual model of the mouthpiece with a virtual model of the first dental anatomy, and with a virtual model of the second dental anatomy. The method may also include visualization data including a simulation of an insertion path of a virtual model of the dental prosthesis being virtually inserted into a virtual model of the dental cavity.

Another example embodiment is a process for manufacturing a mouthpiece. The process may include (a) receiving in-vitro and/or in-vivo three-dimensional imaging data, such as x-ray, ultrasonic, MRT data, intra-oral scans, alginate or silicone impressions, digitized data, and any combination thereof, describing the shape of anatomical structures of a patient's dentition; (b) receiving three-dimensional implant design data, such as CAD, CAM, IGES, STEP, STL, pixel, spline, NURBS, triangle, and voxel data; (c) deriving first three-dimensional design data from the three-dimensional imaging data; (d) deriving second three-dimensional design data from the received three-dimensional implant design data; (e) combining the first and the second three-dimensional design data to form a combined three-dimensional design; (f) deriving numerical control data from the first three-dimensional design data, second three-dimensional design data, and/or the combined three-dimensional design; and (g) shaping the mouthpiece or a part thereof at least partially responsive to the numerical control data. Two-dimensional and three-dimensional imaging and design data can be calibrated, scaled, zoomed, and/or distorted to account for imaging, measurement and manufacturing tolerances and/or shrinking processes during manufacturing. Indirect manufacturing technologies may utilize process steps of inverting two-dimensional or three dimensional shape or contour data. Subsets of the aforementioned process steps can be employed and the ordering of the process steps can be changed. All the foregoing process steps can be combined in any combination.

The mouthpiece and parts thereof can be shaped directly by additive and subtractive manufacturing technologies that include traditional shaping, computer or numerically controlled machinery, shape forming technologies, rapid prototyping technologies, and 3D-printing technologies. Alternatively, indirect manufacturing technologies can be employed, where a substantially negative shape of the mouthpiece or parts thereof is/are fabricated as a mold by additive and subtractive manufacturing technologies that include traditional shaping, computer or numerically controlled machinery, shape forming technologies, rapid prototyping technologies, 3D-printing technologies, and casting technologies.

The mold is then employed to shape the mouthpiece by a casting process. Powders can be pressed and shaped in "green" body stages, pre-sintered or shaped in "white" body stages and further sintered to make the mouthpiece. Positive casting bodies can be made by any or a combination of the foregoing technologies and lost-wax, or other lost-body casting can be employed making the mouthpiece. The mouthpiece can be designed and made in one or more parts and can be assembled. Different materials and technologies can be used to make the different parts. Parts can be bonded, cemented, fixed mechanically (either by a screw or an interlocking surface), or they can be fabricated from a workpiece that is already including different materials.

The mouthpiece can consist of stiff and/or elastic biocompatible materials. Elastic materials of the mouthpiece or parts thereof may have an advantage to distribute the biting and/or inserting forces, making them more spread out, and could account for manufacturing tolerances. Elastic materials and/or designs can be used to make shapes and surfaces of the mouthpiece to fit to the crowns of the adjacent tooth or teeth and/or of the opponent tooth or teeth, and/or onto the prosthesis or parts thereof with compression or a snap, or clip on functionality. The mouthpiece or parts thereof can be made of metal, alloys, plastics, elastics, rubbers, composites, ceramics, cements, including but not limited to PMMA, titanium, Y-TZP ceramics, and silicones.

The push-in implant root can be manually inserted, positioned and oriented and slightly pushed in, to keep temporarily the position and orientation, while the mouthpiece is placed atop of the implant and in correct position and orientation with respect to the opponent and/or adjacent tooth or teeth. The patient may use muscular mastication forces to close the bite and to further engage the mouthpiece and further push in the implant into its bone socket. Additionally, or alternatively, the doctor or assistant may use his or her muscular forces to close the bite and to further engage the mouthpiece and further push in the implant into its bone socket. The mouthpiece can be designed and made to engage the dental anatomy of the upper and of the lower jaw, so that closing the bite will result in a further engagement of the dental anatomy of the upper and of the lower jaw, so that the upper and the lower jaw will be guided and/or centered in a pre-designed orientation and/or position, guiding the implant into a pre-designed orientation and/or position when inserting the implant into its final place. The length of the insertion travel path can be between about 0.1 mm and about 25 mm, preferably greater than about 2 mm.

The engagement amount of the interface surface of the mouthpiece with either or both of the upper or the lower dental anatomy, including the crown or crowns of the tooth or the teeth adjacent the implant position and the crown or crowns of the tooth or the teeth opposite to the implant position is between about 0.01 mm and about 15 mm, preferably on the order of magnitude of about 5 mm in the direction of insertion or engagement. The engagement of the mouthpiece with the implant or prosthesis can utilize an interface surface having a shape and size to align the implant or prosthesis with the mouthpiece. The interface surface can be integrated in a protrusion portion of the mouthpiece. The engagement of the interface surface of the mouthpiece and the occlusal-facing portion or surface of the implant, or of an abutment, or a crown that is integral with the implant is between about 0.01 mm and 15 mm, preferably in the order of magnitude of about 5 mm in the direction of the insertion path of such implant. The term "engagement with" shall include the control of a spatial position with up to three degrees of translational freedom or directions, and/or the control of spatial orientations or inclinations with up to three degrees of rotational freedom or orientations.

The design of the mouthpiece can include process steps that account for a pre-defined insertion path and/or a pre-defined final implant position and/or orientation in relation to the shape of the bone socket and the adjacent dental anatomy, including at least one adjacent crown. The design of the mouthpiece can include process steps that account for a pre-defined bite relation between the upper and the lower jaw, for example in centric occlusion. The design process can include the process step to derive a spatial or translational upper/lower jaw relation from the imaging data received.

The mouthpiece may cover one or more adjacent and/or opponent crowns, a portion of a quadrant, a portion of the entire dentition or the entire dentition. The main dimensions of the mouthpiece are between about 2 mm and 70 mm in each of the sagittal, transversal, and frontal direction of the human anatomy. A typical embodiment has a length of about 40 mm, a width of about 15 mm and a height of about 15 mm. An optional handle for the person assisting with the insertion of the implant is assembled to or integral with the mouthpiece.

The various embodiments of this invention described herein are not only substitutive, but additive to the available options in the field of restorative and prosthetic dentistry with the result that in most cases the need to use removable dentures will be significantly postponed.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

The aforementioned views and schematics are two-dimensional representations of three-dimensional physical objects, to the extent that the two-dimensional drawings indicating side views, cross-sections and/or shadows of surfaces indicating a third dimension. All two-dimensional and three-dimensional shapes and contours that are visualized symmetrically include asymmetric embodiments and vice versa, all shapes and contours that are shown two-dimensionally describe embodiments that have symmetric and or asymmetric shapes and contour extensions in the third dimension not shown.

DETAILED DESCRIPTION

The present invention will now be described more fully hereinafter with reference to the accompanying drawings, which illustrate embodiments of the invention. The invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments.

Figure 1:
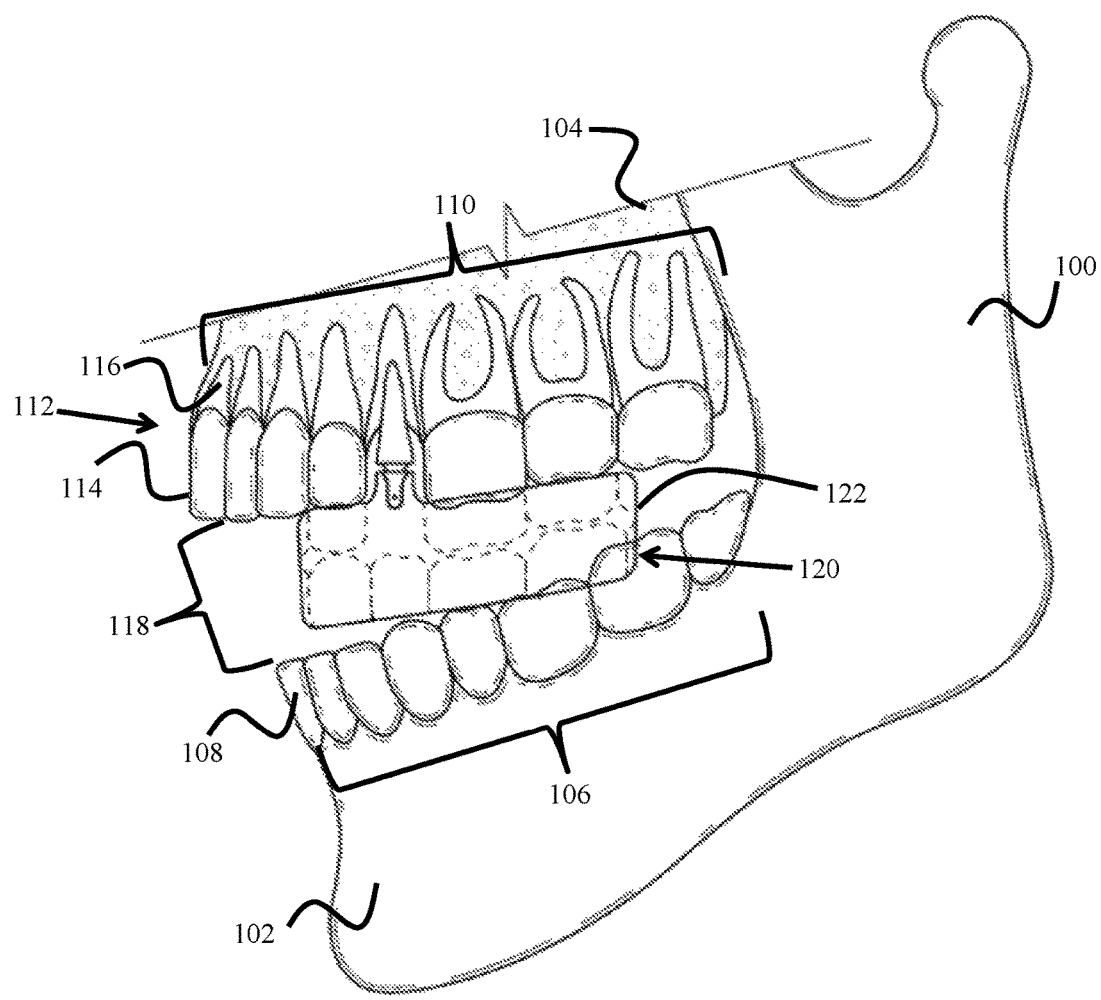
FIG. 1 is a side perspective view of a mouthpiece disposed in an open jawbone of a patient for securing and inserting a dental implant root portion into the jawbone of the patient.

Referring now to FIG. 1, a side perspective view is shown of a mouthpiece disposed in an open jawbone of a patient for securing and inserting a dental implant root portion into the jawbone of the patient. A patient's jaw 100 includes a lower jawbone 102 and upper jawbone 104. The lower jawbone 102 includes a lower dentition 106 comprising lower dental elements 108. Lower dental elements 108 can include any one of or any combination of the patient's natural teeth, including natural roots and crowns, artificial dental prostheses, including artificial roots, crowns, and bridges, and/or temporary dental support structures disposed in the lower jawbone 102.

Similarly, the upper jawbone 104 includes an upper dentition 110 comprising upper dental elements 112. Upper dental elements 112 can include any one of or any combination of the patient's natural teeth, including natural roots and crowns, artificial dental prostheses, including artificial roots, crowns, and bridges, and/or temporary dental support structures disposed in the upper jawbone 104. For example, an upper dental element 112 can include a crown 114 and a root portion 116. As shown in FIG. 1, there is a space, opening, or gap 118 disposed between lower dental elements 108 and upper dental elements 112 when the patient's jaw 100 is open, either being held open by the patient or a dentist or similar practitioner.

A mouthpiece 120 is shown to be disposed in space 118 between upper dentition 110 and lower dentition 106. Mouthpiece 120 comprises a support structure 122 for securing and inserting a dental implant root portion into the jawbone of the patient, described further with regard to FIG. 2 as follows. Support structure 122, in some embodiments, can hold patient's jaw 100 open to support space 118.

Figure 2:
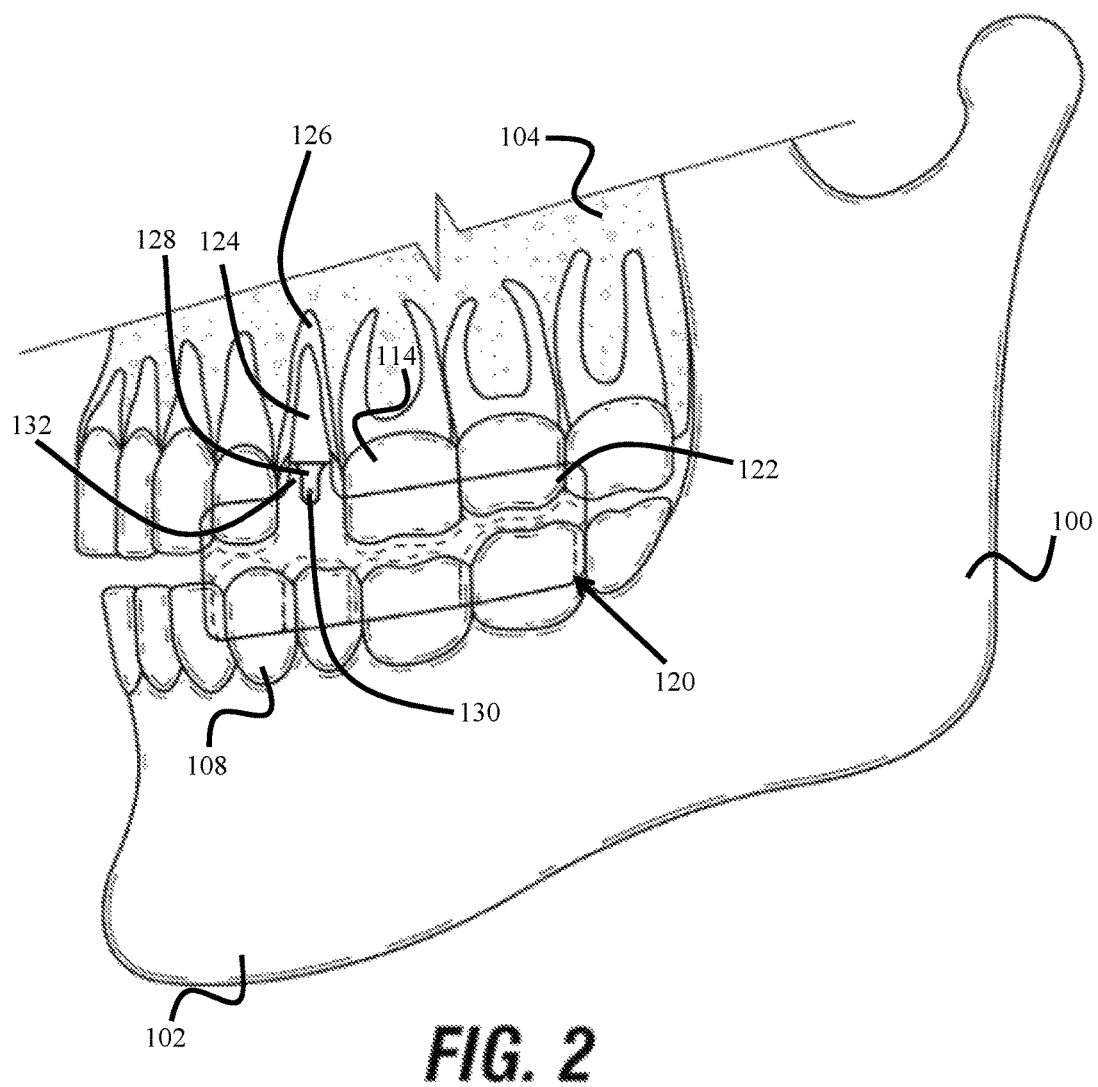
FIG. 2 is a side perspective view of a mouthpiece disposed in a partially-open jawbone of a patient for securing and inserting a dental implant root portion into the jawbone of the patient.

Referring now to FIG. 2, a side perspective view is shown of mouthpiece 120 disposed in the partially-open jaw 100 of the patient for securing and inserting a dental implant root portion 124 into the upper jawbone 104 of the patient. Dental implant root portion 124 is secured into a cavity 126 in the upper jawbone 104 of the patient, for example for osseointegration, as the patient's jaw 100 is closed, or in other words, as lower jawbone 102 and upper jawbone 104 are brought together, either by the patient and/or by the dentist or similar practitioner. Dental implant root portion 124 includes an abutment 128 with a position indicator 130. For example, abutment 128 is engagingly seated with a protrusion 132 on support structure 122 that extends upwardly beyond support structure 122, substantially perpendicular to a horizontal plane formed by the support structure 122 (discussed further with regard to FIG. 4 below).

Abutment 128 can comprise either or both of a generic shape and a three-dimensional custom shape for fitting a crown or other prosthetic component. Generic shapes are, for example, conical, cylindrical, and hexagon shapes or shapes with indexes. Three-dimensional custom shapes are, for example, asymmetrically sized, shaped and extended free-form surfaces, such as preparation posts of a natural tooth ground down by a dentist to receive a crown. Cavity 126 is prepared for osseointegration of dental implant root portion 124. As shown by the dotted lines in FIGS. 1 and 2, the interior of support structure 122 is custom form-fit to 4 lower dental elements 108 of lower dentition 106 on lower jawbone 102 opposite upper jawbone 104, and the interior of support structure 122 is custom form-fit to 3 upper dental elements 112 on upper jawbone 104 opposite lower jawbone 102.

The interior of support structure 122 is custom form-fit to 2 adjacent upper dental elements 112 adjacent to cavity 126 on either side of cavity 126, and the interior of support structure 122 is custom form-fit to a third upper dental element spaced apart from, but located on the same jawbone as cavity 126. In the embodiments shown, the upper and lower dental elements are crowns of teeth, either natural or prosthetic. In other embodiments, dental elements adjacent and opposite a cavity for custom form-fitting by the support structure of a mouthpiece can include any other dental structure such as an abutment, or temporary dental structures. In other embodiments, the interior of a mouthpiece need not be form-fit, but can be made of a pliable or soft material to engage dental structures proximate a cavity when an upper jaw and lower jaw are brought together.

The interior shape of a support structure of a mouthpiece of the present disclosure can be wholly generic, wholly custom shaped, or partially generic and partially custom shaped. For instance, in vivo imaging data can be used to custom form-fit the support structure to dental structures adjacent to the cavity, dental structures opposite to the cavity, and any other dental structures in the mouth of a patient. In vivo imaging data can be acquired by x-ray scanning the mouth of a patient or by taking physical molds of the mouth of a patient, for example, before or after removal of a tooth to be replaced by a prosthesis. Mouthpiece 120 can be formed from and include any one of or any combination of plastic, metal, rubber, and composite materials. Moreover, a mouthpiece with custom shapes and/or generic shapes can be formed from subtractive manufacturing processes such as those using computer numerical control ("CNC") machines, and from additive processes such as injection molding and 3-D printing.

Figure 3:
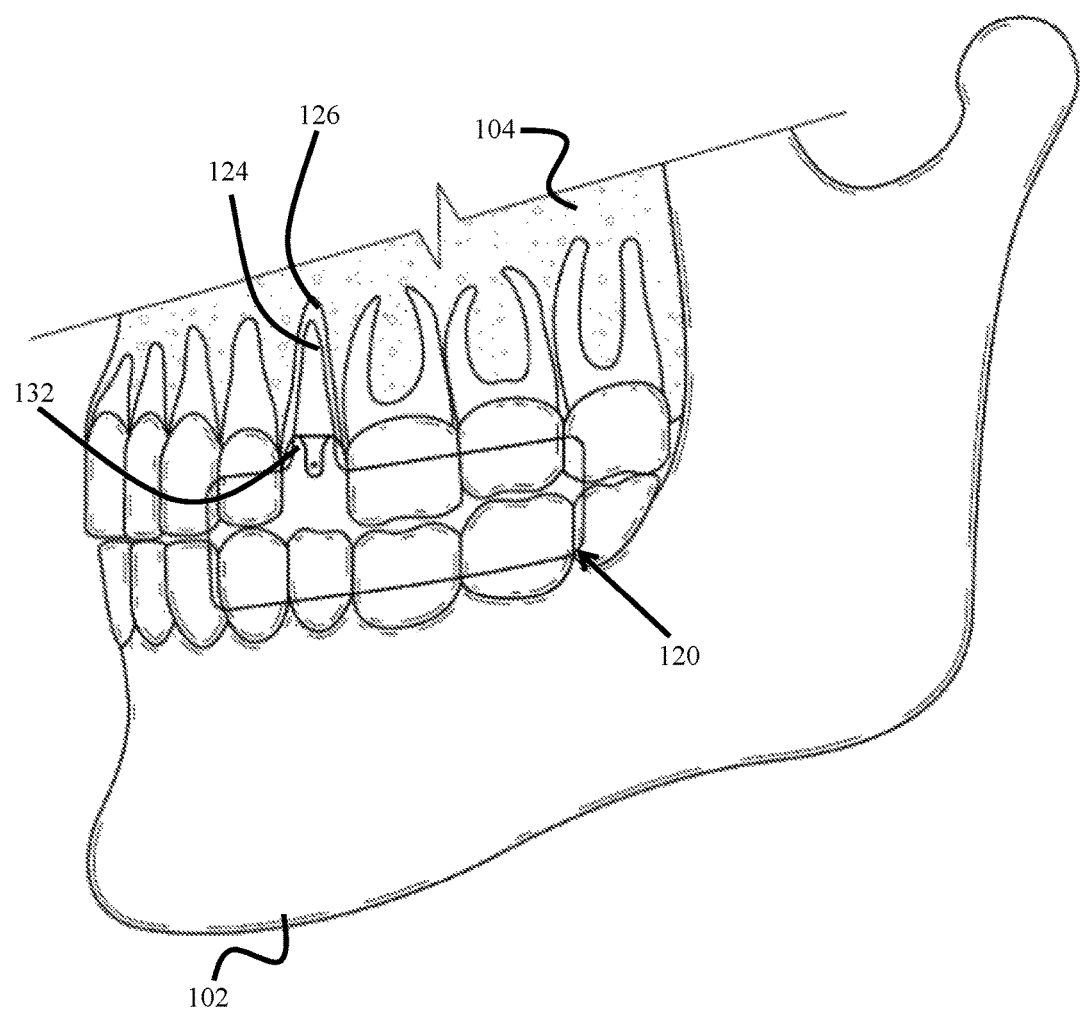
FIG. 3 is a side perspective view of a mouthpiece disposed in a closed jawbone of a patient for securing and inserting a dental implant root portion into the jawbone of the patient.

Referring now to FIG. 3, a side perspective view is shown of a mouthpiece disposed in a closed jawbone of a patient for securing and inserting a dental implant root portion into the jawbone of the patient. When space 118 from FIG. 1 is eliminated or partially eliminated by the closure or partial closure of lower jawbone 102 and upper jawbone 104, mouthpiece 120 securely inserts dental implant root portion 124 into cavity 126 by upward motion of protrusion 132, optionally for temporary placement or permanent placement and osseointegration. While the embodiments of FIGS. 1-3 have been described with regard to placing a dental implant root portion in upper jawbone 104, a dental implant root portion could similarly be placed in lower jawbone 102 by the systems and methods described.

Moreover, while the embodiments of FIGS. 1-3 show the secure placement of one single-root dental implant root portion, multiple adjacent or spaced apart dental implant root portions could be placed at once with an appropriately configured mouthpiece with multiple adjacent or spaced apart protrusions extending beyond the support structure. Protrusions for use in the present disclosure can extend toward a cavity and/or away from a cavity into which a dental implant root portion will be placed, substantially perpendicular to a horizontal plane extending outwardly from the support structure. Additionally, the systems and methods of the present disclosure successfully apply to dental prosthesis with single-rooted dental implant root portions and multi-rooted dental implant root portions (i.e. those root portions corresponding with multiple cavities in the jawbone).

Figure 4:
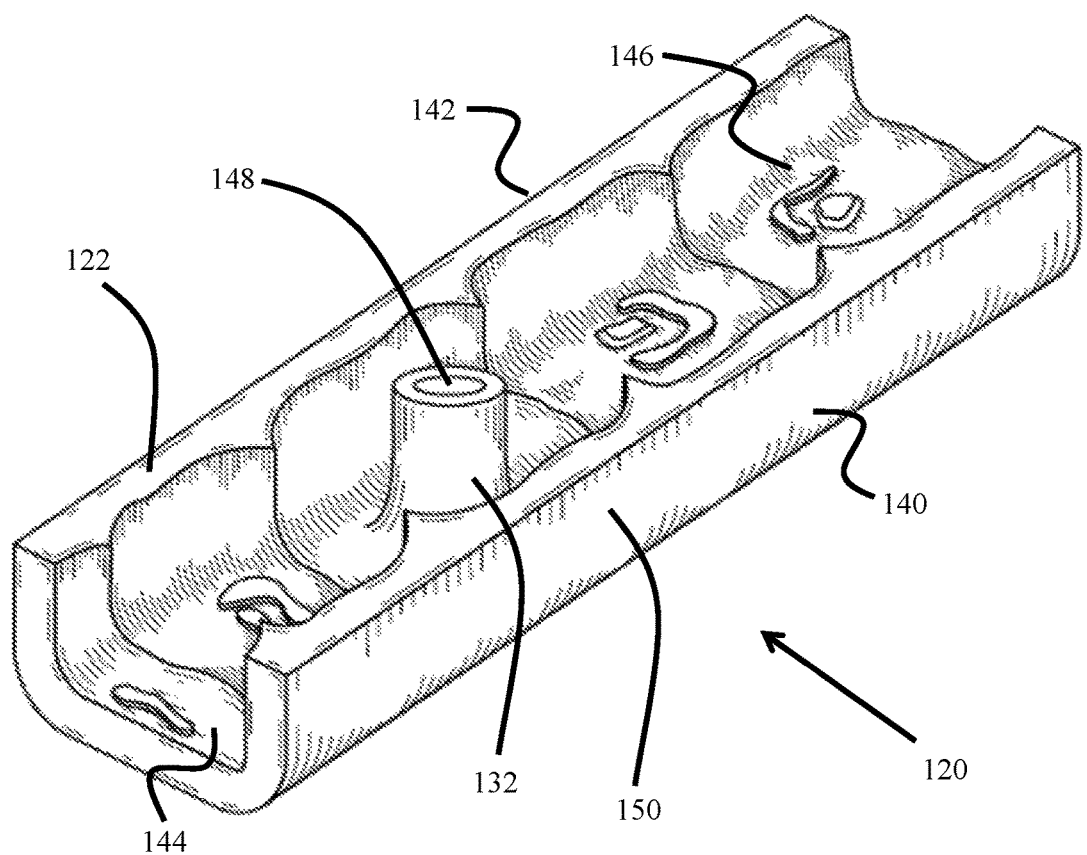
FIG. 4 is an upper side perspective view of a mouthpiece for securing and inserting a dental implant root portion into the jawbone of the patient.

FIG. 4 is an upper side perspective view of a mouthpiece for securing and inserting a dental implant root portion into the jawbone of the patient. Mouthpiece 120 includes support structure 122, which itself includes a vestibular support 140, a lingual support 142, and an occlusal support 144. Together, vestibular support 140, lingual support 142, and occlusal support 144 partially or wholly encompass or surround dental components proximate a jawbone cavity into which a dental implant root portion is to be securely placed. For example, vestibular support 140, lingual support 142, and occlusal support 144 encompass certain upper dental elements 112 in FIGS. 1-3 proximate cavity 126. Vestibular support 140, lingual support 142, and occlusal support 144 form openings 146 which engage with dental elements, such as for example upper dental elements 112, for securely placing dental implant root portion 124 into cavity 126.

Further with respect to FIG. 4, the openings 146 formed by the vestibular support 140, the lingual support 142, and the occlusal support 144 show occlusal and interproximal build ups that would fit into the occlusal and interproximal surfaces of the upper dental elements 112 and define a form-fit and therefore a defined position in mesial and distal direction between the entire mouthpiece 120 and upper dental elements 112. The process of engaging the surfaces of the openings 146 and the upper dental elements 112 provides a successive form-fit guidance aligning the mouthpiece 120 with the upper dental elements 112.

The guidance includes a successive reduction of the spatial degrees of freedom that includes three translational directions (for example x, y, and z axes) and three rotational directions (for example, a rotation around x, a rotation around y, and a rotation round z axes). With respect to FIGS. 1 and 2, the lower jawbone 102 includes a lower dentition 106 comprising lower dental elements 108 which engage with respective openings (opposite 146) formed by a vestibular support, a lingual support, and a occlusal support which have occlusal and interproximal build ups that would fit into the occlusal and interproximal surfaces of the lower dental elements 108 and define a form-fit and therefore a defined position in mesial and distal direction between the entire mouthpiece 120 and lower dental elements 108. The process of engaging the surfaces of the openings (opposite 146) and the lower dental elements 108 provides a successive form-fit guidance aligning the mouthpiece 120 with the lower dental elements 108. The guidance includes a successive reduction of the spatial degrees of freedom that includes three translational directions (for example x, y, and z axes) and three rotational directions (for example, a rotation around x, a rotation around y, and a rotation round z axes). FIG. 2 shows an "aligned bite" situation between the upper dental elements 112 and the lower dental elements 108.

In the embodiment of FIG. 4, openings 146 are custom form-fit to engage a specific patient's pre-existing dental elements proximate the cavity into which a dental implant root portion will be securely placed. In other embodiments, however, openings 146 need not be custom shaped to fit a patient's pre-existing dental elements, but instead may be generically-shaped or partially-custom-shaped. In some embodiments, support structure 122 is formed from a malleable or semi-malleable material, such as for example rubbery, expandable material, that forms around and securely engages around a patient's pre-existing dental elements proximate a cavity into which a dental implant root portion will be securely placed.

Support structure 122 includes protrusion 132 which extends outwardly from and beyond support structure 122. In the embodiment shown, protrusion 132 is generally-cylindrically shaped and integrally/monolithically formed with support structure 122. Protrusion 132 arises out of occlusal support 144 toward a cavity, such as cavity 126, into which a dental implant root portion, such as, for example dental implant root portion 124, would be securely placed. However, in other embodiments, a protrusion need not be generally-cylindrically shaped, and can be of any suitable shape for securely placing the root portion of a dental implant. Moreover, the protrusion need not be integrally/monolithically formed with the support structure and can be separately formed and connected to a support structure as required for insertion of a dental implant root portion.

Additionally, in other embodiments, a protrusion may arise outwardly and extend beyond the support structure from the vestibular support 140 and/or the lingual support 142 rather than, or in addition to, from occlusal support 144. Additionally, any one or all of vestibular support 140, lingual support 142, and occlusal support 144 are optional, and the only support required is that which positions a protrusion necessary for insertion of dental implant root portion 124 into cavity 126 (for example, see FIG. 13).

Protrusion 132 includes a generally-cylindrically shaped recess 148 which engages with abutment 128 in the embodiment of FIGS. 1-3. Recess 148 need not be generally-cylindrically shaped, and in other embodiments can be any shape necessary to engage with a dental implant prosthesis to securely place a dental implant root portion into a cavity. For example, a recess in a protrusion can be custom form-fit to engage a custom formed dental implant. Or, for example, a recess in a protrusion can be custom form-fit to engage a crown of a one piece dental prosthesis. For example, the protrusion 132 can be shaped to fill the entire space the of the openings 146 directly atop of the cavity 126, which is the extraction void of the former crown between the directly adjacent crowns. In this embodiment, the protrusion directly engages with surfaces of the adjacent crown(s) mesial and/or distal to the dental cavity 126.

The recess 148 can have a negative size and shape of a three-dimensional custom shape of the abutment 128, including for example, asymmetrically sized, shaped and extended free-form surfaces, such as preparation posts of a natural tooth ground down by a dentist. In this case the vestibular, mesial, distal and oral facing surfaces of the walls of the recess 148 form an interface that engages and aligns the respectively sized and shaped portion of the abutment 128. The form-fit aligns the mouthpiece 120 with the entire dental prosthesis. The alignment includes a reduction of the spatial degrees of freedom between the mouthpiece and the entire dental prosthesis that includes three translational directions (for example x, y, and z axes) and three rotational directions (for example, a rotation around x, a rotation around y, and a rotation round z axes), or a subset of that.

In the embodiment of FIG. 4, the support structure 122 is formed so as to custom form-fit around and engage three upper dental elements 112 on upper dentition 110 proximate cavity 126. In addition, and as shown in FIGS. 1-3, support structure 122 can have a lower support structure to custom form-fit and engage around lower dental elements 108 in lower dentition 106. A lower support structure can also have vestibular and lingual supports in some embodiments. However, a lower support structure is not required to have vestibular and lingual supports, and instead an occlusal support, such as occlusal support 144 can be custom form-fit to pre-existing dental elements in the patient's mouth on both sides facing both the upper jawbone, such as upper jawbone 104, and the lower jawbone, such as lower jawbone 102. For example, an outer surface 150 of support structure 122 can also be partially or wholly custom form-fit to pre-existing dental structures in a patient's mouth.

However, in other embodiments, any number of dental elements in either or both of a patient's upper or lower jaw may be generically fit or custom form-fit by the support structure, so long as proper support is provided for the protrusion to securely place and dispose the dental implant root portion into a cavity.

A key can be made in analogy to the embodiment shown in FIG. 4 that includes a cut out portion to the vestibular so that the fit of the openings 146 with the dental elements 112 and the fit of the recess 148 with the abutment 128 is visible to the person that assists with the insertion.

Figure 5:
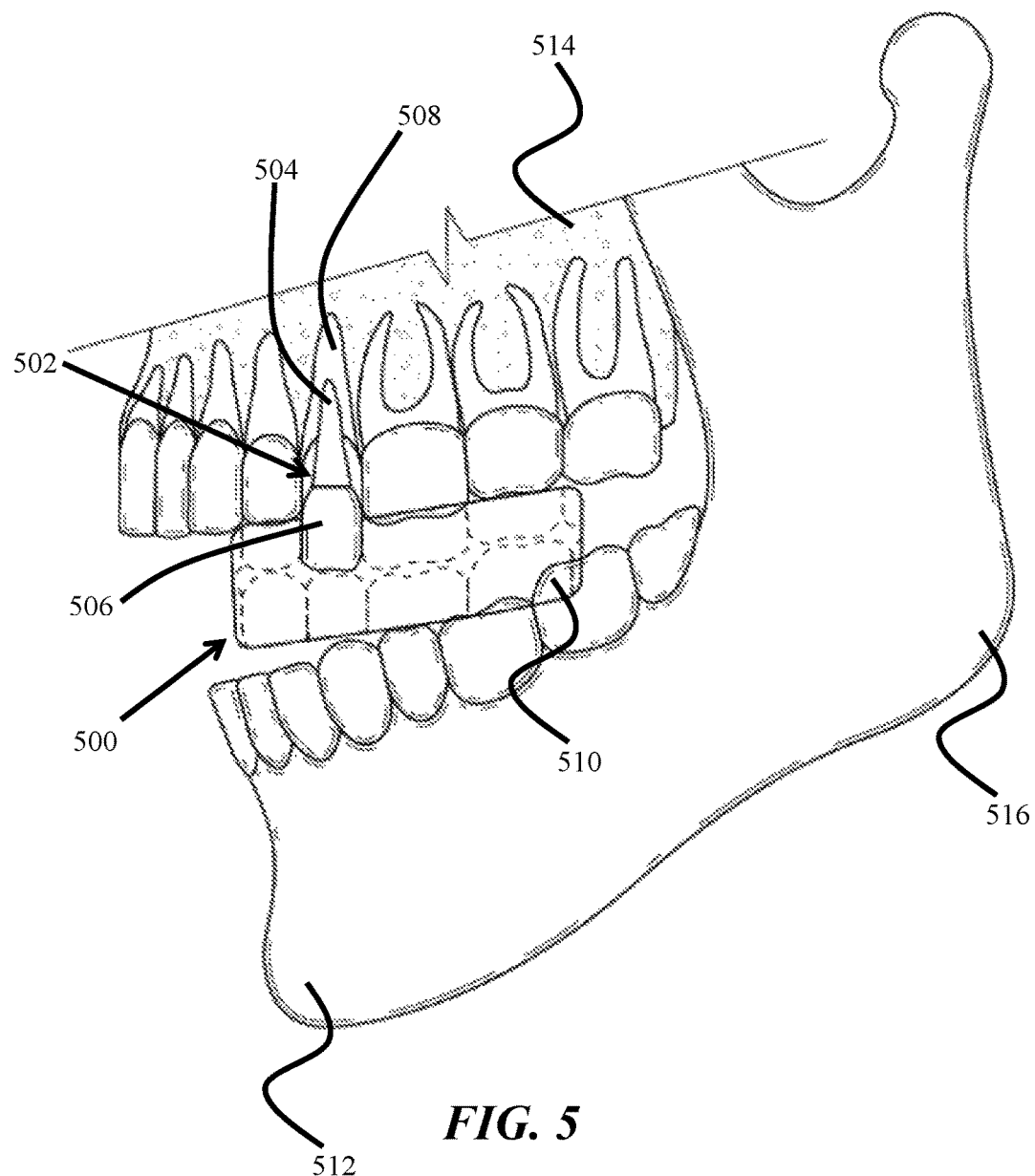
FIG. 5 is a side perspective view of a mouthpiece disposed in an open jawbone of a patient for securing and inserting a one-piece dental tooth prosthesis into the jawbone of the patient.

Referring now to FIG. 5, a side perspective view is shown of a mouthpiece disposed in an open jawbone of a patient for securing and inserting a one-piece dental tooth prosthesis into the jawbone of the patient. A mouthpiece 500 is shown with a custom form-fit to a crown 506 of a one-piece dental implant 502, which itself also includes a dental implant root portion 504. When the jaw 516 of the patient is wholly or partially closed, mouthpiece 500 securely places or disposes dental implant root portion 504 into cavity 508 for either temporary placement or permanent placement and osseointegration.

In the embodiment of FIG. 5, a support structure 510 custom form-fits certain pre-existing dental structures of the patient adjacent to and opposite the cavity 508 (shown by dotted lines). One or more partially and/or wholly generically and/or custom form-fit shaped protrusions, optionally with one or more partially and/or wholly generically and/or custom form-fit shaped recesses, extending outwardly from support structure 510 (not shown) engage and stabilize crown 506 during the insertion of one-piece dental implant 502 into cavity 508.

Figure 6:
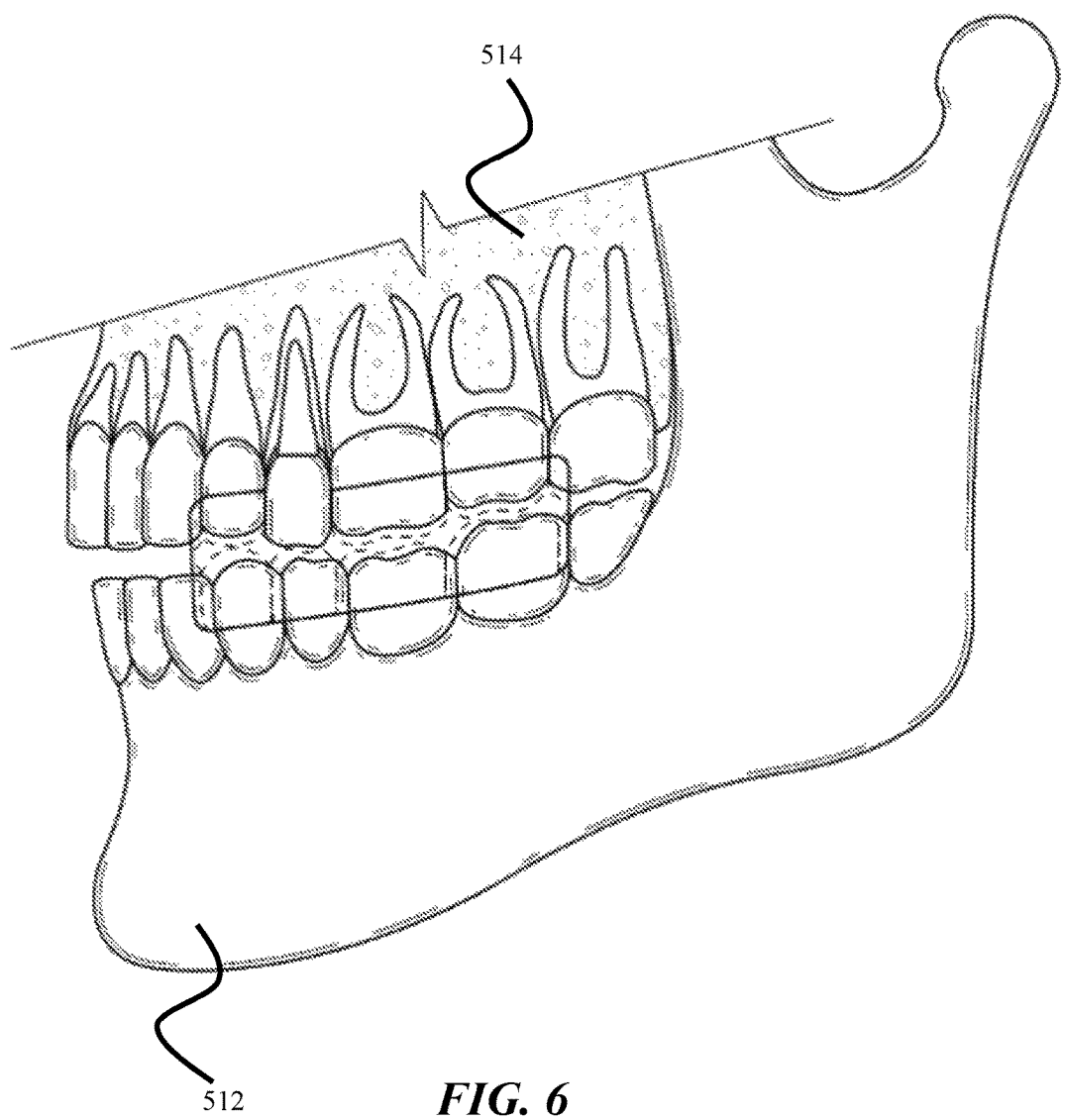
FIG. 6 is a side perspective view of a mouthpiece disposed in a partially-open jawbone of a patient for securing and inserting a one-piece dental tooth prosthesis into the jawbone of the patient.
Figure 7:
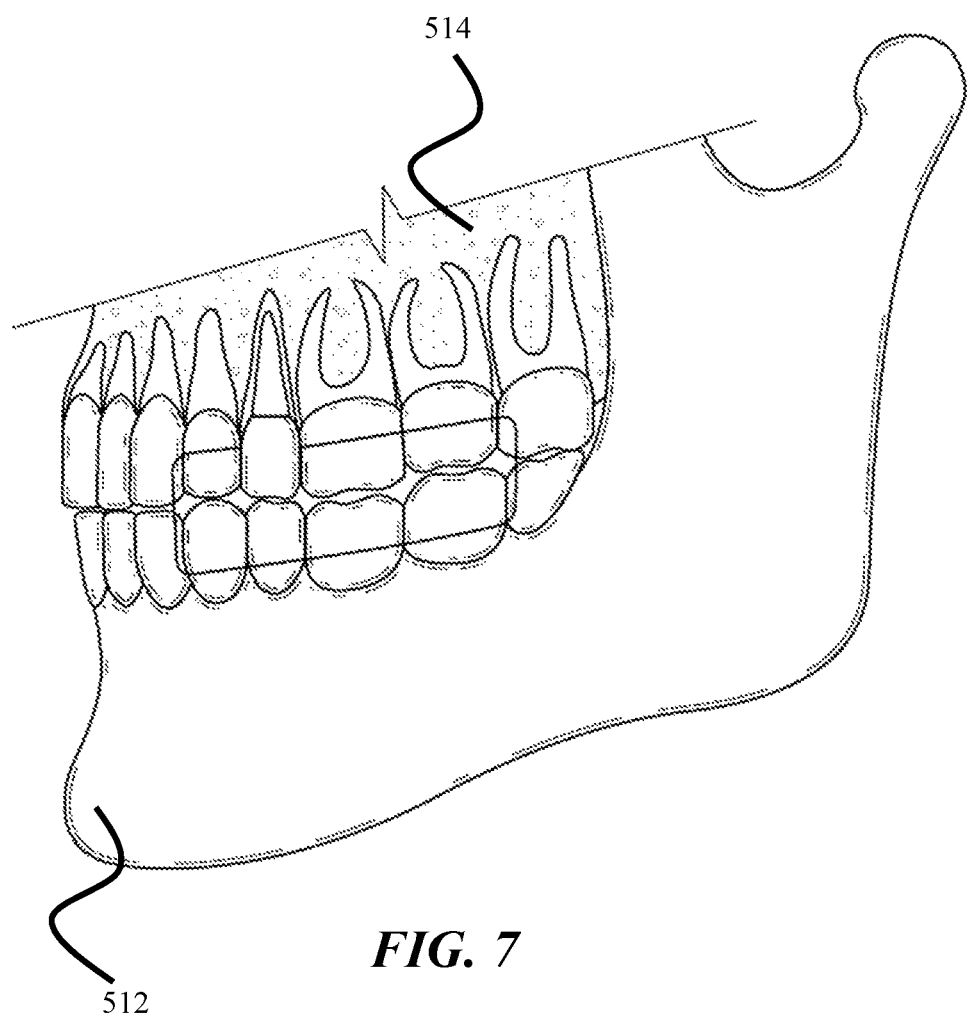
FIG. 7 is a side perspective view of a mouthpiece disposed in a closed jawbone of a patient for securing and inserting a one-piece dental tooth prosthesis into the jawbone of the patient.

Referring now to FIG. 6, a side perspective view is shown of a mouthpiece disposed in a partially-open jawbone of a patient for securing and inserting a one-piece dental tooth prosthesis into the jawbone of the patient. FIG. 6 shows the embodiment of FIG. 5 as a lower jawbone 512 and an upper jawbone 514 of the patient are brought together. FIG. 7 is a side perspective view of a mouthpiece disposed in a closed jawbone of a patient for securing and inserting a one-piece dental tooth prosthesis into the jawbone of the patient. FIG. 7 shows the embodiment of FIG. 5 when the lower jawbone 512 and the upper jawbone 514 of the patient are closed.

Figure 8:
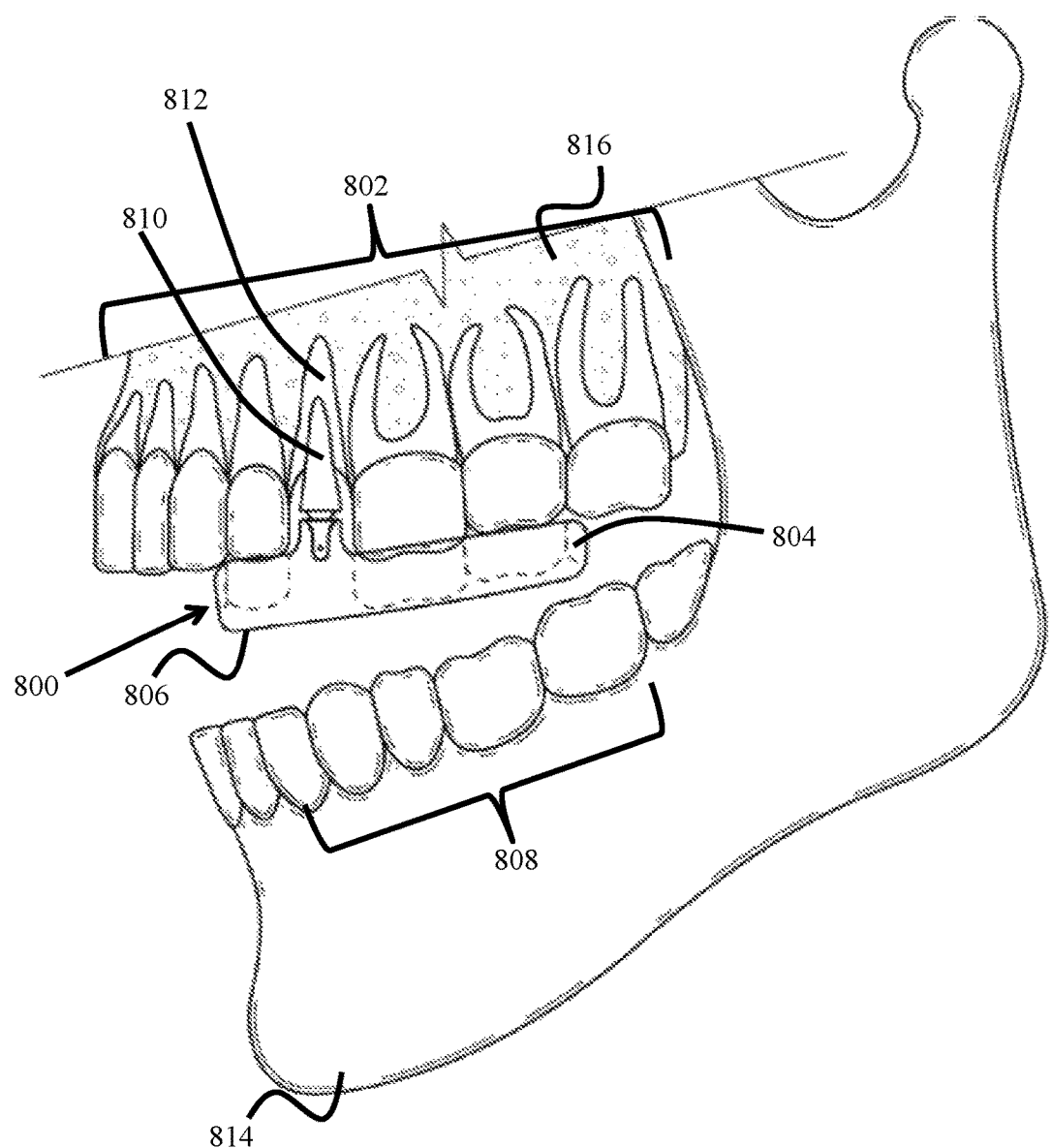
FIG. 8 is a side perspective view of an upper-dentition mouthpiece disposed in an open jawbone of a patient for securing and inserting a dental implant root portion into the jawbone of the patient.

Referring now to FIG. 8, a side perspective view is shown of an upper-dentition mouthpiece disposed in an open jawbone of a patient for securing and inserting a dental implant root portion into the jawbone of the patient. Upper-dentition mouthpiece 800 of FIG. 8 is similar to that of mouthpiece 120 in FIG. 1; however, as can be seen, upper-dentition mouthpiece 800 is only custom form-fit to certain pre-existing dental elements in upper dentition 802, as shown by the dotted lines. A support structure 804 of upper-dentition mouthpiece 800 has a soft or malleable underside 806, such that when lower pre-existing dental elements 808 contact underside 806, the upper-dentition mouthpiece 800 slightly deforms for comfortable insertion of dental implant root portion 810 into cavity 812. As noted previously, while the systems and methods of the present disclose have been discussed with respect to secure placement of a dental implant in the upper jawbone of a patient, all embodiments of systems and methods apply to similar placement of a dental implant in a lower jawbone of a patient.

Figure 9:
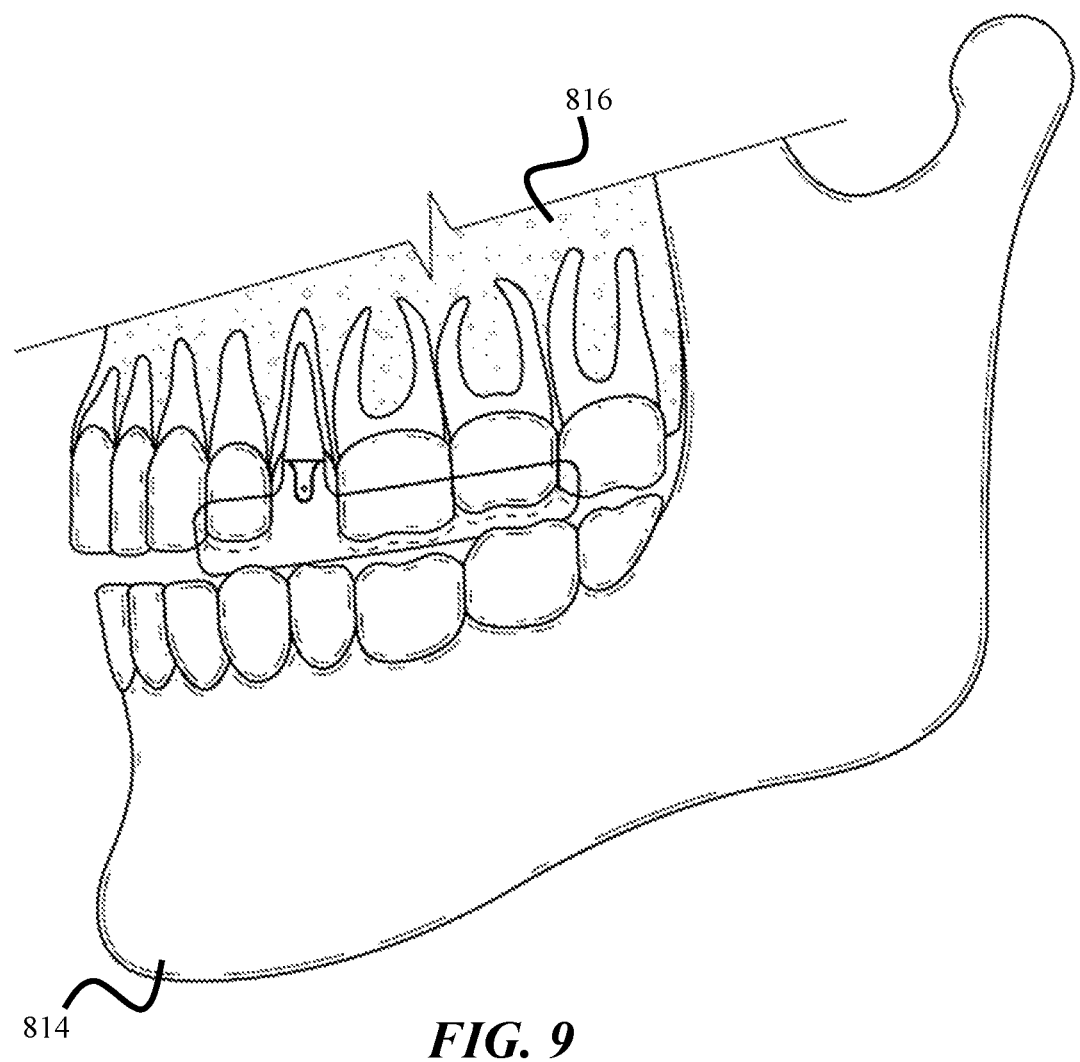
FIG. 9 is a side perspective view of an upper-dentition mouthpiece disposed in a partially-open jawbone of a patient for securing and inserting a dental implant root portion into the jawbone of the patient.

FIG. 9 is a side perspective view of an upper-dentition mouthpiece disposed in a partially-open jawbone of a patient for securing and inserting a dental implant root portion into the jawbone of the patient. FIG. 9 shows the embodiment of FIG. 8 when a lower jawbone 814 and upper jawbone 816 of the patient's mouth are brought together.

Figure 10:
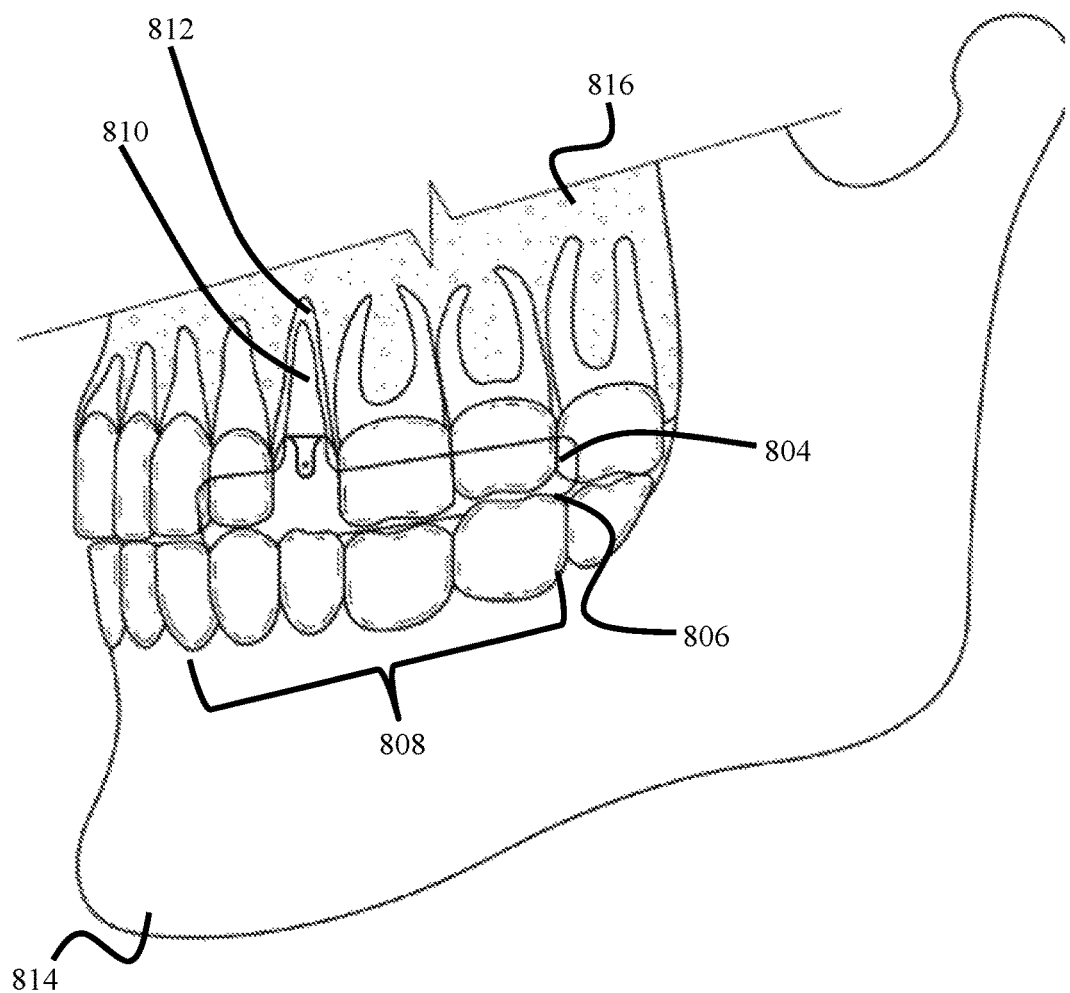
FIG. 10 is a side perspective view of an upper-dentition mouthpiece disposed in a closed jawbone of a patient for securing and inserting a dental implant root portion into the jawbone of the patient.

Referring now to FIG. 10, a side perspective view is shown of an upper-dentition mouthpiece disposed in a closed jawbone of a patient for securing and inserting a dental implant root portion into the jawbone of the patient. FIG. 10 shows the embodiment of FIG. 9 when the lower jawbone 814 and upper jawbone 816 of the patient's mouth are closed. Underside 806 as shown is slightly deformed or molded around lower pre-existing dental elements 808 when the patient's jaw is closed for insertion of dental implant root portion 810 into cavity 812.

In some embodiments, a portion of or all of support structure 804 can remain in the patient's mouth for some amount of time to allow for the osseointegration of the dental implant root portion 810 after the lower jawbone 814 and upper jawbone 816 are brought together. For example, in some embodiments, some or all of support structure 804 could be glued to some or all of upper dentition 802 to support osseointegration of dental implant root portion 810 into cavity 812. A protrusion and support structure can provide stability during either or both of dental implant surgery and osseointegration. Moreover, in some embodiments not shown, a dental implant root portion and/or a cavity can include chevron fins or other anchoring or osseointegration structures, surfaces, and/or chemical preparations.

For example, referring to the embodiment of FIG. 4, after dental implant surgery to securely place a dental implant root portion, a vestibular support, a lingual support, and/or an occlusal support could be removed from the mouth of a patient while leaving behind one or more supports to support the protrusion which would anchor and stabilize a dental implant root portion during osseointegration.

Figure 11:
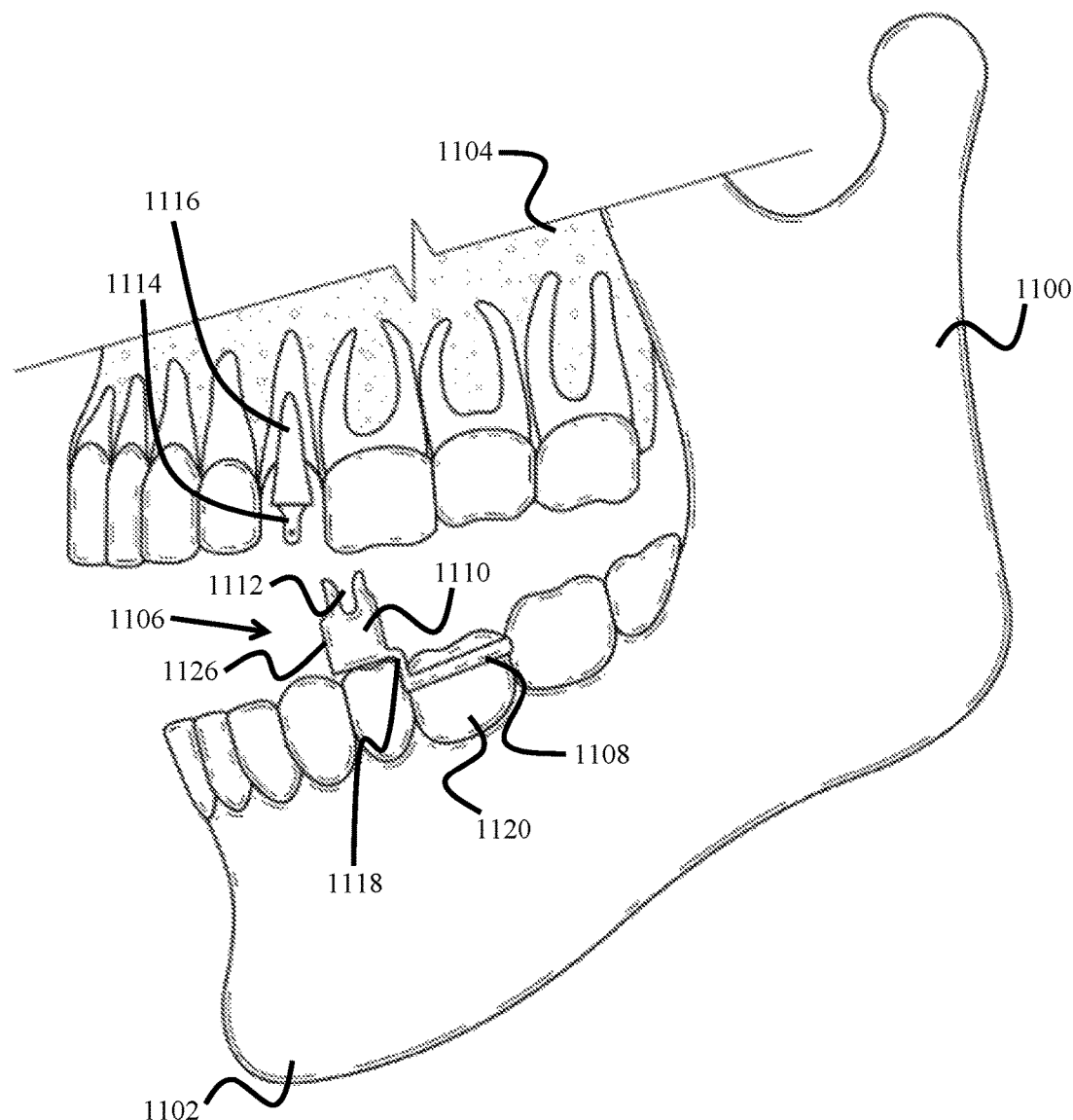
FIG. 11 is a side perspective view of a lower-dentition mouthpiece disposed in an open jawbone of a patient for securing and inserting a dental implant root portion into an upper jawbone of the patient.

FIG. 11 is a side perspective view of a lower-dentition mouthpiece disposed in an open jawbone of a patient for securing and inserting a dental implant root portion into an upper jawbone of the patient. A patient's jaw 1100 includes a lower jawbone 1102 and an upper jawbone 1104. A mouthpiece 1106 is pictured, with a support structure 1108 and a protrusion 1110. Protrusion 1110 includes a recess 1112 for engaging abutment 1114 of dental implant root portion 1116. Protrusion 1110 is connected to support structure 1108 by a connector 1118. In the embodiment of FIG. 11, support structure 1108 includes a band or cap that fits around a crown 1120 of a tooth, the tooth being either natural or prosthetic. The support structure 1108 can be either a custom fit band or cap, for example partially or wholly custom form fit as a substantial negative of the shape of the crown 1120, or the support structure 1108 can be a generic shape made of an expandable or formable material to securely fit around and engage crown 1120.

Figure 12:
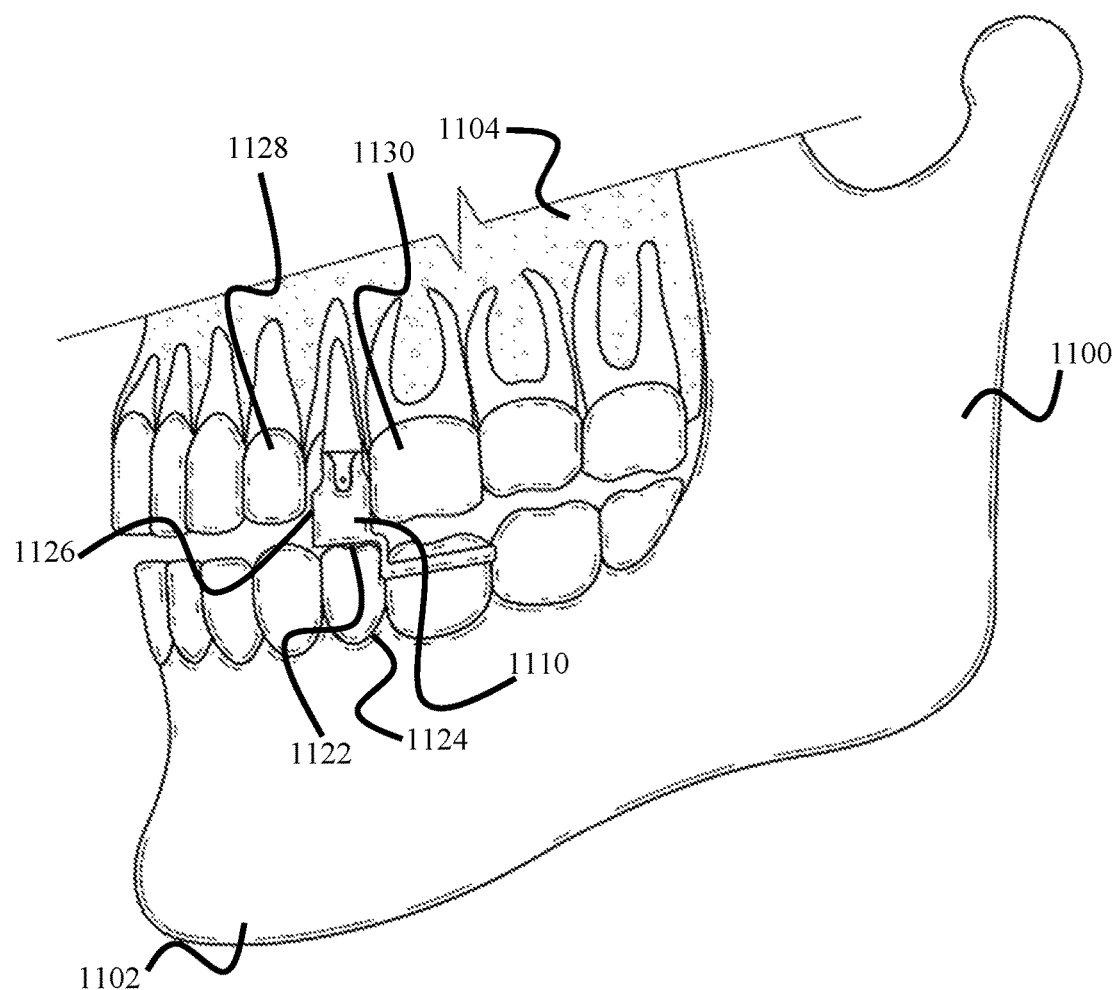
FIG. 12 is a side perspective view of a lower-dentition mouthpiece disposed in a partially-open jawbone of a patient for securing and inserting a dental implant root portion into an upper jawbone of the patient.

FIG. 12 is a side perspective view of a lower-dentition mouthpiece disposed in a partially-open jawbone of a patient for securing and inserting a dental implant root portion into an upper jawbone of the patient. FIG. 12 shows the embodiment of FIG. 11 as the patient's lower jawbone 1102 and upper jawbone 1104 are brought together. A lower occlusal surface 1122 of protrusion 1110 rests on crown 1124 as lower jawbone 1102 and upper jawbone 1104 are brought together. In the embodiment of FIGS. 11 and 12, recess 1112 is shown to be a generic shape to engage with abutment 1114, which is also a generic shape. However, recess 1112 in other embodiments can be custom form-fit to engage a custom shape abutment or a custom shaped crown. Moreover, an external surface 1126 of protrusion 1110 is shown in FIGS. 11 and 12 to be a generic, generally-cylindrical shape. However, in other embodiments, an external surface of a protrusion can be custom form-fit to fit between crowns, such as crowns 1128, 1130 in FIG. 12. In such an embodiment, the external surface of the protrusion can be shaped to have a substantial negative shape of the crowns 1128, 1130.

Figure 13:
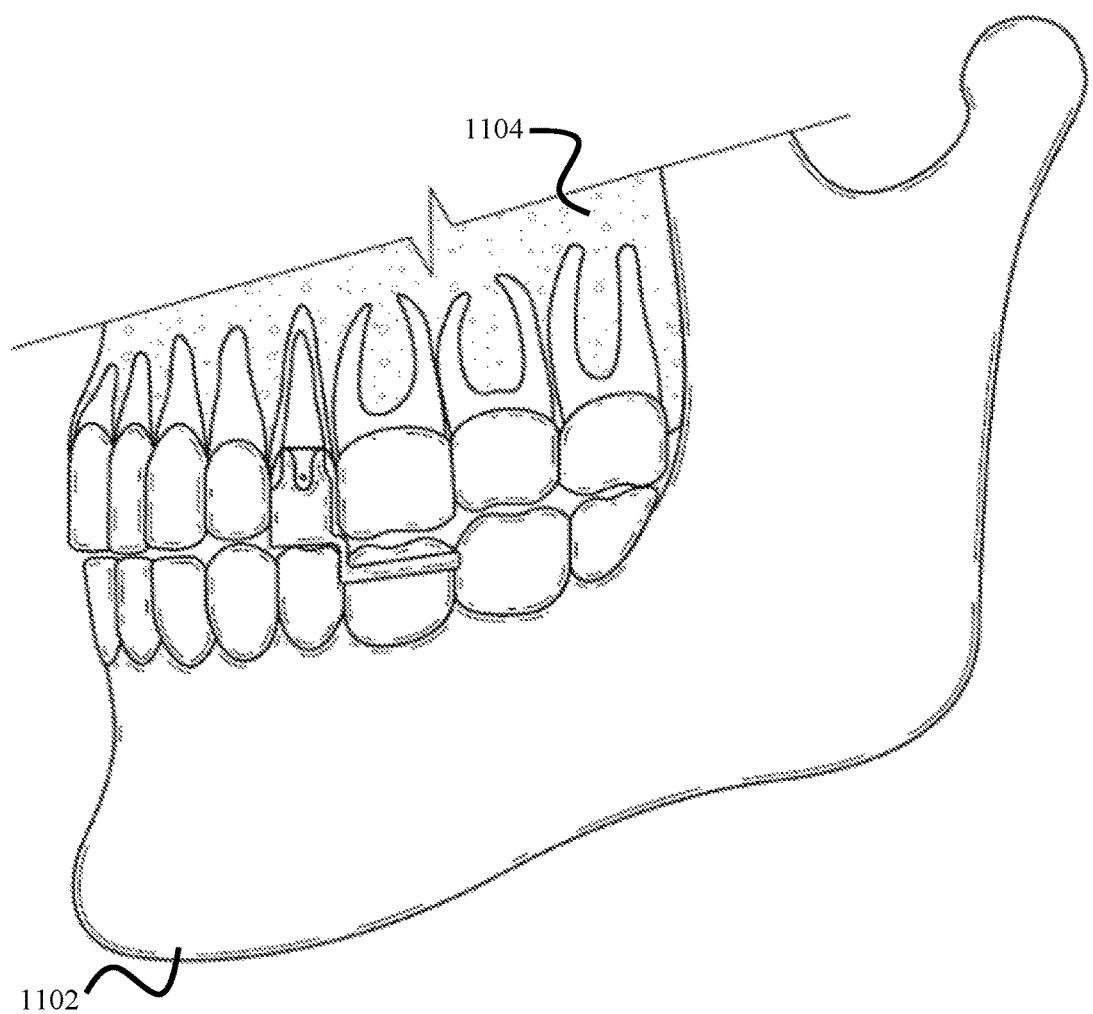
FIG. 13 is a side perspective view of a lower-dentition mouthpiece disposed in a closed jawbone of a patient for securing and inserting a dental implant root portion into an upper jawbone of the patient.

FIG. 13 is a side perspective view of a lower-dentition mouthpiece disposed in a closed jawbone of a patient for securing and inserting a dental implant root portion into an upper jawbone of the patient. FIG. 13 shows the embodiment of FIG. 11 when the patient's lower jawbone 1102 and upper jawbone 1104 are substantially closed.

Figure 14:
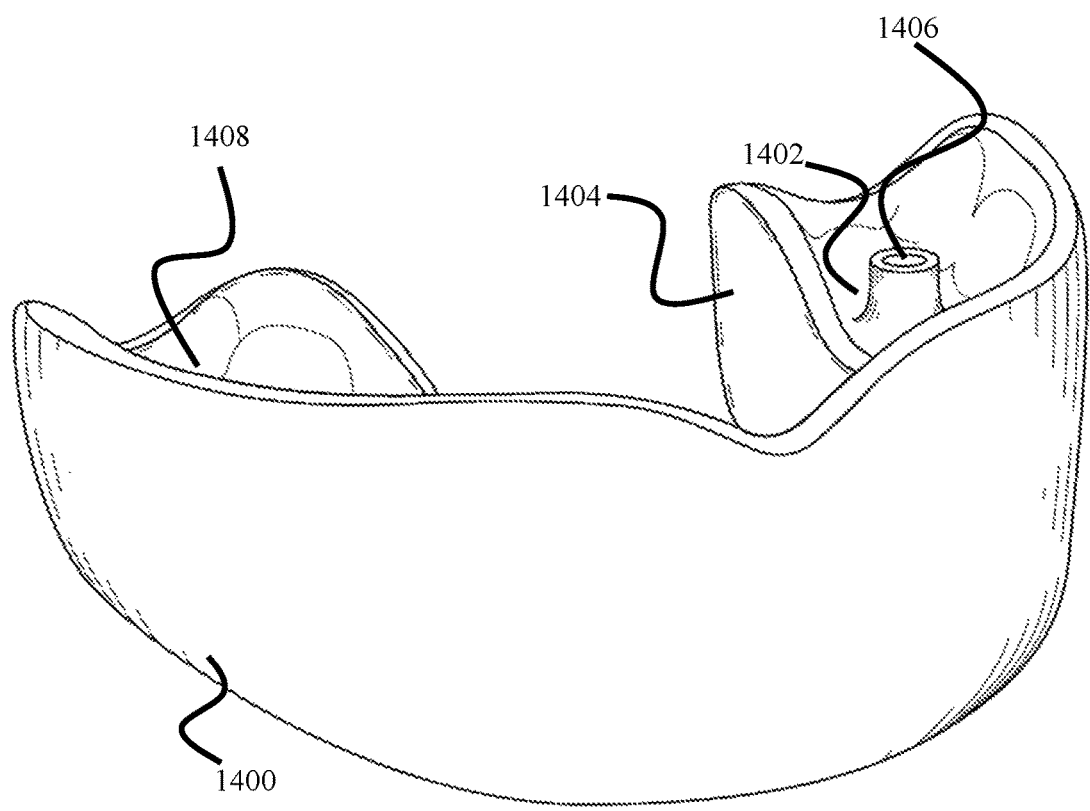
FIG. 14 is an upper front perspective view of a mouthpiece for securing and inserting a dental implant root portion into the jawbone of the patient.

FIG. 14 is an upper front perspective view of a mouthpiece for securing and inserting a dental implant root portion into the jawbone of the patient. Mouthpiece 1400 includes a protrusion 1402 and a support structure 1404. Protrusion 1402 includes a generally-cylindrical recess 1406 for engaging the abutment of a dental implant root portion. While the embodiment of FIG. 14 shows the protrusion 1402 with the recess 1406 generally generically shaped and integral/monolithic with support structure 1404, in other embodiments the protrusion 1402 and recess 1406 can be partially or wholly custom form fit to form the substantial negative of a custom implant abutment portion or a custom implant crown portion. Moreover, the protrusion can be a separate piece and attachable and detachable from the support structure, in some embodiments.

Support structure 1404 includes a dental element canal 1408 to wrap around and encompass a patient's pre-existing dental structures in the mouth. Dental element canal 1408 can be partially or wholly generically shaped or custom form-fit shaped. In vivo imaging data, scan data, or data acquired from a mold can be used to form support structure 1404 including dental element canal 1408 and/or protrusion 1402 with recess 1406.

In some embodiments of the systems and methods, no recess is required on a protrusion, for example in FIG. 14, if recess 1406 were not present, protrusion 1402 could press against an abutment or crown sufficiently to securely insert it into the jawbone of a patient. The material of which either support structure 1404 and/or protrusion 1402 are made can be hard and non-deformable, soft and slightly deformable, or soft and highly deformable. The material can include plastic, metal, foam, rubber, composite materials, and any combination thereof to create a mouthpiece of sufficient hardness and comfort for a patient.

The embodiments visualized in FIGS. 1-3, and 5-13 with respect to the three-dimensional size and shape of the dental implant root portion 124, 504, 810, 1116 and the three-dimensional size and shape of the dental cavity 126, 508, 812 are for better understanding simplified, but shall include each an alternative embodiment where a press-fit is realized to that the implant root portion is sized and shaped to engage with the dental cavity tightly by means of bone compression and surface friction.

Miscellaneous

One of ordinary skill in the art will recognize that various aspects of the inventions as explained above can readily be combined with each other.

The meaning of "CAD" shall include but shall not be limited to any and all technology of computer aided design.

The meaning of "CAM" shall include but shall not be limited to any and all technology of computer aided manufacturing.

The meaning of "CNC" shall include but shall not be limited to any and all technology of computer numerical control as it relates to manufacturing machinery and systems, including but not limited to rapid prototyping devices and systems.

The meaning of "rapid prototyping" shall include but shall not be limited to all technologies qualified for manufacturing of copies of virtual three-dimensional objects and also technologies qualified for mass customization or the mass production of copies of customized or adapted geometries to the needs of an individual patient. Rapid prototyping in this context shall include but not be limited to manufacturing technologies based on the digital data, by a process that includes depositing material, in accordance with the digital data, layer-by-layer in a plurality of layers each constituting a two-dimensional cross section of a solid object having an edge defined by data of the three-dimensional surface, the layers being stacked in a third dimension to form the solid object having a three-dimensional surface defined by the data. All such rapid prototyping technologies can be used directly to manufacture the part of interest, for example, by selective laser sintering or indirectly by fabricating first, e.g., a resin or wax sample of the part of interest and second using for example, "lost-wax" casing to duplicate such sample and fabricate therewith the part of interest. It also includes sintering techniques where the "green" body is printed in response to computerized numerical controlled (CNC) data and then sintered to its final material properties. Sintering in this context includes pressure and heat.

The meaning of "rapid prototyping" shall be used in its broadest technical sense, where individualized parts are made from virtual representations, and shall include respective additive, subtractive and forming technologies used to three-dimensionally shape work pieces. The meaning of "additive shaping" shall include but shall not be limited to selective laser melting, selective laser sintering, stereolithography, 3-D printing or depositing of wax, wax-bound powders, adhesive-bound powders, slurries. The meaning of "subtractive shaping" shall include but shall not be limited to 3D laser shaping, CNC-grinding, CNC-turning, and CNC-milling technologies, and other machining and finishing technologies. The meaning of "shape forming" shall include but shall not be limited to near net-shape forming technologies, CNC-stamping, and CNC-pressing and casting technologies.

The meaning of "prosthesis" shall include any substantially artificially shaped part of any natural and artificial material. In this sense a dental prosthesis for perio-type integration would have to be distinguished to any human tooth used for intentional re-implantation.

Whenever the context requires, the word "prosthesis" shall be deemed to include the word "implant" and vice versa.

"3D" shall mean three-dimensional.

The meaning of "CT" shall include but shall not be limited to any and all technology of computed tomography.

"CBCT" shall mean cone beam computed tomography and shall include "DVT" technology.

"DVT" shall mean digital volume tomography.

"Three-dimensional X-ray image" shall include but shall not be limited to voxel data, volumetric X-ray data, at least two two-dimensional X-ray images in DICOM format, a stack of two-dimensional X-ray images, data received from CBCT or other CT, MRT, ultrasonic and TOF devices, or any combination thereof.

The meaning of "MRT" shall include but shall not be limited to any and all technology of magnetic resonance tomography.

The meaning of "TOF" shall include but shall not be limited to any and all technology employing Time-of-Flight procedures.

The meaning of "imaging" and "scanning" shall include but shall not be limited to any and all technology of acquiring two-dimensional and/or three-dimensional data of physical objects or parts of a human body.

The meaning of clinical "imaging data" shall include but shall not be limited to in-vivo and in-vitro processes that result in any anatomical data of the anatomy of a human being. In this context the term data shall include but shall not be limited to two-dimensional and three-dimensional data.

The meaning of three-dimensional data shall include but shall not be limited to surface (e.g., triangulated data) and volumetric (e.g., voxel) data.

The meaning of "perio-type tissue" and "periodontal tissue" shall include but shall not be limited to any soft tissue surrounding a tooth.

The meaning of "perio-type ligature", "perio-type ligament", "periodontal ligature", "ligament", or "periodontal ligament" shall include but shall not be limited to the fibrous connective tissue interface usually located between a human tooth and the anatomical structure of the jaw of a human being.

The meaning of "cavity" shall include but shall not be limited to the periodontal cavity, a cavity of the jaw bone structure, a cavity of the alveolus or a combination thereof.

The meaning of "extraction socket" shall include prepared or unprepared extraction sockets. The meaning of "prepared" shall include but shall not be limited to being surgically pared, abraded, scraped or curetted by mechanical instruments or laser technology based devices.

The meaning of "replacement", "to replace", "to be replaced" shall include but shall not be limited to any substitution, where one object fills the former position of another object. In the context of the foregoing such substitution can be performed at any time, so that for example, the term replacement shall not be limited to a replacement in a timely manner.

The meaning of a "manufactured one-piece" object shall not be limited to homogeneous objects, and shall include but shall not be limited to manufactured assemblies, objects that are coated, objects that are consisting of more than one pieces or materials bonded together or any combination thereof.

The meaning of a "clinical one-step" process or a "clinical one-step" method shall include but shall not be limited to a series clinical process or method steps performed in one or more clinical events as long as no further iteration is required that includes clinical process or method steps and process or method steps that cannot be performed chair-side.

The meaning of "immediate load" of an implant shall include but shall not be limited to any all integration concepts of implants where the occlusal portion of the implant (e.g., the crown portion facing the opponent jaw) is not protected against the alternate load of mastication by additional protective means.

In dentistry, the term occlusion is used to refer to the manner in which the teeth from upper and lower arches come together when the mouth is closed. The meaning of "occlusion" shall mean but shall not be limited to the manner the teeth of the upper or lower arch are fitting and coming in contact with each other while the mouth is closed or during chewing (articulation). It shall also include the fit and contact of adjacent teeth within one arch. The meaning of "integrated into the occlusion" shall include but shall not be limited to the configuration and integration of the fit and contact situation of a prosthesis within the existing or new build occlusion within the same and the opponent arch.

The words used in this specification to describe the invention and its various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word itself.

The various embodiments and aspects of embodiments of the invention disclosed herein are to be understood not only in the order and context specifically described in this specification, but to include any order and any combination thereof. Whenever the context requires, all words used in the singular number shall be deemed to include the plural and vice versa. Whenever the context requires, all options that are listed with the word "and" shall be deemed to include the world "or" and vice versa, and any combination thereof. The titles of the sections of this specification and the sectioning of the text in separated paragraphs are for convenience of reference only and are not to be considered in construing this specification.

Insubstantial changes from the claimed subject matter as viewed by a person with ordinary skill in the art, now known or later devised, are expressly contemplated as being equivalent within the scope of the claims. Therefore, obvious substitutions now or later known to one with ordinary skill in the art are defined to be within the scope of the defined elements.

In the drawings and specification, there have been disclosed embodiments of the invention, and although specific terms are employed, the terms are used in a descriptive sense only and not for purposes of limitation, the scope of the invention being set forth in the following claims. It must be understood that the illustrated embodiment has been set forth only for the purposes of example and that it should not be taken as limiting the invention. It will be apparent to those skilled in the art that alterations, other embodiments, improvements, details and uses can be made consistent with the letter and spirit of the disclosure herein and within the scope of this disclosure patent, which is limited only by the following claims, construed in accordance with the patent law, including the doctrine of equivalents.

In the drawings and specification, there have been disclosed a plurality of embodiments of the present invention. The applicant would like to emphasize that each feature of each embodiment may be combined with or added to any other of the embodiments in order to modify the respective embodiment and create additional embodiments. These additional embodiments form a part of the present disclosure and, therefore, the applicant may file further patent claims regarding these additional embodiments at a later stage of the prosecution.

Further, the applicant would like to emphasize that each feature of each of the following dependent claims may be combined with any of the present independent claims (regardless of the present claim structure). Therefore, the applicant may direct further patent claims towards other claim combinations at a later stage of the prosecution.

What is claimed is:

1. A mouthpiece for inserting and securing a dental implant root portion in a jawbone of a patient, the mouthpiece comprising:
   a protrusion, wherein the protrusion is configured to engage with at least a portion of a dental tooth prosthesis when the dental tooth prosthesis is placed proximate a dental cavity into which the dental tooth prosthesis will be secured, and wherein the dental tooth prosthesis comprises the dental implant root portion;
   a support structure, wherein the support structure is engaged with the protrusion, wherein the support structure is configured to engage at least one dental structure selected from the group consisting of: a first dental structure on the upper jawbone of the patient and a second dental structure on the lower jawbone of the patient, in the patient's mouth when an upper jawbone and lower jawbone of the patient are spaced apart allowing for space between the first dental structure and the second dental structure, wherein the support structure stably supports the protrusion when the upper jawbone and lower jawbone are brought together,
   wherein the protrusion extends outwardly from the support structure toward an occlusally-facing surface of an abutment of the dental tooth prosthesis to engagingly seat the occlusally-facing surface of the abutment, and wherein the mouthpiece is configured to securely insert the dental implant root portion into the jawbone of the patient when the upper jawbone and lower jawbone are brought together by the protrusion pushing the abutment of the dental tooth prosthesis toward the jawbone of the patient into which the dental implant root is to be implanted.

2. The mouthpiece according to claim 1, wherein the protrusion forms a form-locking fit with the occlusally-facing surface of the abutment, the protrusion comprising a recessed portion shaped as a substantial negative of the occlusally-facing surface.

3. The mouthpiece according to claim 1, wherein the protrusion and the support structure are monolithically formed as one piece.

4. The mouthpiece according to claim 1, wherein the support structure is configured to engage at least one crown located on the same jawbone of the dental cavity where the dental tooth prosthesis will be secured is located.

5. The mouthpiece according to claim 1, wherein the support structure is configured to engage at least one crown adjacent to the dental cavity into which the dental tooth prosthesis will be secured.

6. The mouthpiece according to claim 5, wherein the support structure is custom form-fitted to engage the at least one crown.

7. The mouthpiece according to claim 1, wherein the support structure is configured to engage at least one crown located in the jawbone opposite the jawbone in which the dental cavity, where the dental tooth prosthesis will be secured is located.

8. The mouthpiece according to claim 7, wherein the support structure is configured to align the protrusion with the dental tooth prosthesis.

9. The mouthpiece according to claim 8, wherein the support structure is custom form-fitted to engage the at least one crown.

10. The mouthpiece according to claim 1, wherein the support structure is configured to engage both the first dental structure and the second dental structure.

11. The mouthpiece according to claim 10, wherein the support structure is custom form-fitted to engage both the first dental structure and the second dental structure.

12. The mouthpiece according to claim 1, wherein the support structure substantially matches a dental layout of the patient's mouth, and wherein the support structure is configured to form a form-locking fit with the dental layout of the patient's mouth.

13. A system for dental rehabilitation comprising:
   a dental prosthesis having a push-in type implant root portion to be inserted in a bone cavity of a jawbone of a patient, and
   a mouthpiece for inserting and securing the push-in type implant root portion in the bone cavity, the mouthpiece comprising:
      a first interface portion three-dimensionally sized and shaped to receive an occlusal-facing portion of the dental prosthesis,
      a second interface portion three-dimensionally sized and shaped to receive a first occlusal-facing portion of a first dental anatomy, and
      a third interface portion three-dimensionally sized and shaped to receive forces from a second occlusal-facing portion of a second dental anatomy of a jawbone opposite the dental cavity, the dental prosthesis and the mouthpiece are placed proximate the dental cavity and proximate the second dental anatomy of the jawbone opposite the dental cavity so that the mouthpiece is configured to securely align and insert the dental implant root portion into the jawbone of the patient when the jawbone with the dental cavity and the jawbone opposite the dental cavity are brought together.

14. The system according to claim 13, wherein the third interface portion comprises the second interface portion of the mouthpiece, the second occlusal-facing portion comprises the first occlusal-facing portion, and the second dental anatomy comprises the first dental anatomy, and the first dental anatomy includes at least one crown opponent adjacent the bone cavity.

15. The system according to claim 14, wherein the size and the shape of the second interface portion is configured to guide the mouthpiece when the jawbone with the dental cavity and the jawbone opposite the dental cavity are brought together.

16. The system according to claim 13, wherein second dental anatomy is at least one portion of at least one crown adjacent the dental cavity.

17. The system according to claim 13, wherein the size and the shape of the second interface portion is configured to guide the mouthpiece when the jawbone with the dental cavity and the jawbone opposite the dental cavity are brought together.

18. A mouthpiece for inserting and securing a dental implant root portion in a jawbone of a patient, the mouthpiece comprising:
   a protrusion, wherein the protrusion is configured to engage with at least a portion of a dental tooth prosthesis when the dental tooth prosthesis is placed proximate a dental cavity into which the dental tooth prosthesis will be secured, and wherein the dental tooth prosthesis comprises the dental implant root portion;
   a support structure, wherein the support structure is engaged with the protrusion, wherein the support structure is configured to engage at least one dental structure selected from the group consisting of: a first dental structure on the upper jawbone of the patient and a second dental structure on the lower jawbone of the patient, in the patient's mouth when an upper jawbone and lower jawbone of the patient are spaced apart allowing for space between the first dental and the second dental structure, wherein the support structure stably supports the protrusion when the upper jawbone and lower jawbone are brought together,
   wherein the protrusion extends outwardly from the support structure,
   wherein the protrusion is configured to engage with an occlusally-facing surface of the dental implant root portion of the dental tooth prosthesis,
   wherein the protrusion forms a form-locking fit with the occlusally-facing surface of the dental implant root portion of the dental tooth prosthesis, the protrusion comprising a recessed portion shaped as a substantial negative of the occlusally-facing surface, and
   wherein the mouthpiece is configured to securely insert the dental implant root portion into the jawbone of the patient when the upper jawbone and lower jawbone are brought together.

19. A mouthpiece for inserting and securing a dental implant root portion in a jawbone of a patient, the mouthpiece comprising:
   a protrusion, wherein the protrusion is configured to engage with at least a portion of a dental tooth prosthesis when the dental tooth prosthesis is placed proximate a dental cavity into which the dental tooth prosthesis will be secured, and wherein the dental tooth prosthesis comprises the dental implant root portion;
   a support structure, wherein the support structure is engaged with the protrusion, wherein the support structure is configured to engage both a first dental structure on the upper jawbone of the patient and a second dental structure on the lower jawbone of the patient, in the patient's mouth when an upper jawbone and lower jawbone of the patient are spaced apart allowing for space between the first dental and the second dental structure, wherein the support structure stably supports the protrusion when the upper jawbone and lower jawbone are brought together,
   wherein the protrusion extends outwardly from the support structure, and wherein the mouthpiece is configured to securely insert the dental implant root portion into the jawbone of the patient when the upper jawbone and lower jawbone are brought together.

* * * * *